United States Patent [19]

Yamada et al.

[11] Patent Number: 5,288,852
[45] Date of Patent: Feb. 22, 1994

[54] HUMAN TUMOR NECROSIS FACTOR POLYPEPTIDES

[75] Inventors: Masaaki Yamada, Kyoto; Yasuji Furutani, Toyonaka; Mitsue Notake, Suita; Juniti Yamagishi, Toyonaka, all of Japan

[73] Assignee: Dainippon Pharmaceutical Co., Ltd., Osaka, Japan

[21] Appl. No.: 84,445

[22] Filed: Jul. 1, 1993

Related U.S. Application Data

[60] Continuation of Ser. No. 89,134, Aug. 25, 1987, abandoned, which is a division of Ser. No. 708,846, Mar. 5, 1985, abandoned.

[30] Foreign Application Priority Data

Mar. 6, 1984 [JP] Japan .................................. 59-43617
Apr. 23, 1984 [JP] Japan .................................. 59-82653
Aug. 17, 1984 [JP] Japan .................................. 59-172307

[51] Int. Cl.$^5$ .................... C07K 13/00; A61K 37/02
[52] U.S. Cl. .................................. 530/351; 530/395; 930/144; 424/85.1; 435/69.5; 435/69.7
[58] Field of Search ............... 530/351, 395; 435/69.5, 435/69.7; 424/85.1; 514/2, 8, 12; 930/144

[56] References Cited

U.S. PATENT DOCUMENTS

| | | | |
|---|---|---|---|
| 4,495,282 | 1/1985 | Ohnishi et al. | 530/350 |
| 4,677,063 | 6/1987 | Mark et al. | 435/69.5 |
| 4,677,064 | 6/1987 | Mark et al. | 435/69.1 |
| 4,677,197 | 6/1987 | Lin et al. | 530/417 |
| 4,879,226 | 11/1989 | Wallace et al. | 435/68 |

FOREIGN PATENT DOCUMENTS

| | | |
|---|---|---|
| 0131789 | 1/1985 | European Pat. Off. |
| 0158286 | 10/1985 | European Pat. Off. |
| 0166996 | 1/1986 | European Pat. Off. |
| 0168214 | 1/1986 | European Pat. Off. |
| 0183198 | 6/1986 | European Pat. Off. |
| 60-30688 | 2/1985 | Japan . |
| WO86/02381 | 4/1986 | PCT Int'l Appl. |
| WO86/03751 | 7/1986 | PCT Int'l Appl. |
| WO86/04606 | 8/1986 | PCT Int'l Appl. |

OTHER PUBLICATIONS

Pennica et al., Nature, vol. 312 Dec. 20-27, 1984, pp. 724-728.
Reed et al., The Jour. of Immunology, vol. 115, No. 2, Aug., 1975, pp. 395-404.
Matthews, Immunology, vol. 44, pp. 135-142 (1981).
Williamson et al., Proc. Natl. Acad. Sci. USA, vol. 80, pp. 5397-5401 (Sep., 1983).
Aggarwal et al., The Journal of Biological Chemistry, vol. 260, No. 4, pp. 2345-2354 (Feb., 1985).
Shirai et al., Nature, vol. 313, pp. 803-806 (Feb., 1985).
Williamson et al Proc Natl Acad Sci. vol. 80 (17) pp. 5171-5174 Sep. 1983 "Human tumour necrosis factor: precursor structure, expression and homology to lymphotoxin".

Primary Examiner—Garnette D. Draper
Attorney, Agent, or Firm—Wenderoth, Lind & Ponack

[57] ABSTRACT

A novel cloned DNA encoding a human tumor necrosis factor (TNF), a vector having said DNA inserted thereinto, a host transformed with said vector and a novel human TNF polypeptide, and processes for producing them.

4 Claims, 5 Drawing Sheets

HUMAN TUMOR NECROSIS FACTOR POLYPEPTIDES

This application is a continuation of now abandoned application Ser. No. 07/089,134, filed Aug. 25, 1987, which is a division of now abandoned application Ser. No. 708,846, filed Mar. 5, 1985.

BRIEF DESCRIPTION OF THE INVENTION

The present invention relates to (1) a DNA having or containing a base sequence corresponding to a human tumor necrosis factor polypeptide, its principal portion, or a polypeptide derived from an allelic mutant of the DNA encoding human tumor necrosis factor polypeptide (hereinafter referred to as allelic mutant polypeptide) or a base sequence resulting from modification of said base sequence;

(2) a vector having said DNA inserted thereinto, a host transformed with said vector, a process for producing a polypeptide corresponding to said DNA by using said host;

(3) a polypeptide having or containing a human tumor necrosis factor polypeptide or its principal portion, a human tumor necrosis factor-like substance or its principal portion, or their chemically or enzymatically modified substances; and (4) a pharmaceutical composition containing said polypeptide or substance, or its use as an antitumor agent in patients.

BACKGROUND OF THE INVENTION

Carswell et al. found that the sera of mice infected with bacillus Calmette-Gubrin (BCG) and then treated with endotoxin contain a substance which necrotizes transplanted Meth A sarcoma; and named it tumor necrosis factor (hereinafter referred to as TNF) [Proc. Nat. Acad. Sci., U.S.A., 72, 3666 (1975)).

TNF is considered to be a physiologically active substance released from macrophages, and is known to be characterized in that (i) when it is administered to animals bearing a certain kind of tumor (for example, Meth A sarcoma), it causes necrosis in the tumor and cures the animals; (ii) it has a cytotoxic effect in vitro on a certain kind of tumor cells (such as mouse L cells) but has scarcely any injurious effect on normal cells; and (iii) its activity is not animal species-specific.

Because of these characteristics, it has been strongly desired to develop TNF as a new type of antitumor agent.

TNF or a TNF-like substance has been reported in the following literature references or published in the following patent documents.

Green et al., Proc. Nat. Acad. Sci., U.S.A., 73, 381 (1976).
Matthews et al., Br. J. Cancer, 42, 416 (1980).
Ruff et al., J. Immunol., 125, 1671 (1980).
Männel et al., Infect. Immunity, 28, 204 (1980).
Haranaka et al., Japan. J. Exp. Med., 51, 191 (1981).
European Patent Publication No. 90892.
European Patent Publication No. 86475.
Japanese Patent Publication No. 21621/1983.

The processes disclosed in these documents are characterized by involving purification of TNF from body fluids (e.g., blood) or tissues of rabbits, mice, hamsters or guinea pigs as raw materials. The products, however, are not so clearly defined, and it is evident that various restrictions are imposed on these processes in regard to the supply of raw materials and the purities of the final products.

In clinical application as a potent antitumor agent, TNF originated from humans is desirable in consideration of immunogenicity. The above-described processes, however, cannot be applied to the production of human TNF.

The following have so far been reported on an antitumor cytotoxin originated from humans: cytotoxins produced from human peripheral monocutes and human myelocytic monocytic leukemia cells [Matthews, Immunology, 44, 135 (1981)], from the adherent cells in human peripheral blood cells [Reed, et al., J. Immunol., 115, 395 (1975)], and from human B cell lines [Williamson, et al., Proc. Nat. Acad. Sci., U.S.A., 80, 5397 (1983)). These substances have cytotoxic activity, but are not defined clearly.

DETAILED DESCRIPTION OF THE INVENTION

The present inventors have made various investigations by applying the recombinant DNA technology. These investigations have led to successful cloning of cDNA encoding human TNF polypeptide. In the course of these investigations, the present inventors also found that the human TNF cDNA codes for its precursor polypeptide. Furthermore, the present inventors succeeded in producing human TNF polypeptide in a host transformed with an expression vector having the cloned human TNF cDNA inserted thereinto, and in purifying the human TNF polypeptide to homogeneity.

For simplification of the description, the following abbreviations are used in the present specification and claims.

A: adenine
C: cytosine
G: guanine
T: thymine
Ala: alanine
Arg: arginine
Asn: asparagine
Asp: aspartic acid
Cys: cysteine
Gln: glutamine
Glu: glutamic acid
Gly: glycine
His: histidine
Ile: isoleucine
Leu: leucine
Lys: lysine
Met: methionine
Phe: phenylalanine
Pro: proline
Ser: serine
Thr: threonine
Trp: tryptophan
Tyr: tyrosine
Val: valine
DNA: deoxyribonucleic acid
cDNA: complementary DNA
sscDNA: single-stranded cDNA
dscDNA: double-stranded cDNA
RNA: ribonucleic acid
mRNA: messenger RNA
poly(A)mRNA: poly(A)-containing mRNA
dATP: deoxyadenosine triphosphate
dCTP: deoxycytidine triphosphate dGTP: deoxyguanosine triphosphate
dTTP: deoxythymidine triphosphate
oligo(dC): oligodeoxycytidylic acid
oligo(dG): oligodeoxyguanylic acid
oligo(dT): oligodeoxythymidylic acid
poly(A): polyadenylic acid
poly(U): polyuridylic acid
poly(dC): polydeoxycytidylic acid
poly(dG): polydeoxyguanylic acid
ATP: adenosine triphosphate
EDTA: ethylenediaminetetraacetic acid
kb: kilobases
kbp: kilobase pairs
bp: base pairs
Meth A sarcoma: methylcholanthrene-induced sarcoma
TNF: tumor necrosis factor
rHu-TNF: recombinant human TNF In the present specification, the base sequence shown by a single strand is the base sequence of a sense strand, and the left end is a 5'-terminus and the right end, a 3'-terminus. In the amino acid sequence, the left end is an N-terminus, and the right end, a C-terminus.

A detailed description of the present invention follows together with an account of the background that has led to the present invention.

[I-1] DNA encoding a rabbit TNF and the rabbit TNF

The present inventors made various investigations with an eye on the application of recombinant DNA technology, and then succeeded in cloning cDNA encoding a rabbit TNF and elucidated of what the rabbit TNF is. More specifically, the present inventors cultivated rabbit macrophages in vitro together with suitable inducers, and ascertained that the rabbit TNF was produced and released in the culture medium. Subsequently, the present inventors found cultivation conditions which caused the rabbit TNF mRNA to be produced and accumulated in high concentrations in the macrophages. The present inventors further succeeded in cloning of cDNAs encoding the rabbit TNF and determined their base sequences, and also found that the rabbit TNF is formed as a precursor. Furthermore, the present inventors succeeded in producing the rabbit TNF in a host transformed with an expression vector having the cloned cDNA inserted thereinto.

Details of the above cDNA encoding the rabbit TNF and the rabbit TNF are described, for example, in U.S. patent application Ser. No. 677,680 filed on Nov. 30, 1984 now U.S. Pat. No. 5,043,271 and European Patent Application No. 84114325.8 filed on Nov. 27, 1984. Their main points are briefly described below.

A typical DNA which encodes a mature rabbit TNF is represented by a base sequence represented by formula [1-1] in the attached Table 1-1.

The DNA having a base sequence represented by formula [1-1] encodes a polypeptide represented by formula [1-2] in the attached Table 1-2.

A DNA encoding a rabbit TNF codes for a precursor of the rabbit TNF and a typical DNA encoding the rabbit TNF precursor is represented by formula [2-1] in the attached Table 2-1 or a DNA resulting from the addition of ATG to its 5'-terminus.

The DNA having the base sequence represented by formula [2-1] encodes a polypeptide represented by formula [2-2] in the attached Table 2-2.

A polypeptide having the amino acid sequence represented by the formula [1-2] in Table 1-2 which is the mature rabbit TNF is not species-specific and is useful as an antitumor agent because it has a selective cytotoxic effect on tumor cells and regresses tumors of tumor-bearing animals.

Table 3 shows the base sequence of one example of cDNA where the rabbit TNF is encoded. The base sequence shown in Table 2-1 corresponds to the base sequence from the 37th to 738th bases in Table 3. However, the first 15 bases are an oligo(dg) tail added for insertion of the cDNA into a vector.

[1-2] The DNAs of this invention are DNAs having or containing a base sequence corresponding to a human tumor necrosis factor (human TNF) polypeptide or its principal portion(s), or its allelic mutant polypeptide, or a base sequence resulting from modification of said base sequence, and more specifically DNAs having or containing a base sequence corresponding to an amino acid sequence represented by the following formula [I]

$(Y)_p—(X)_n—(B)_m—A$          [I]

or a base sequence having a termination codon at the 3'-terminus of said base sequence, wherein
A is a polypeptide of the formula [Ia] below in which one or more amino acids may be deleted or replaced by other amino acid(s),
B is a peptide of the formula [Ib] below in which one to three amino acids may be deleted or replaced by other amino acid(s),
X is a polypeptide,
Y is Met, and
m, n and p are 1 or 0;
the formula [Ia] being as follows:

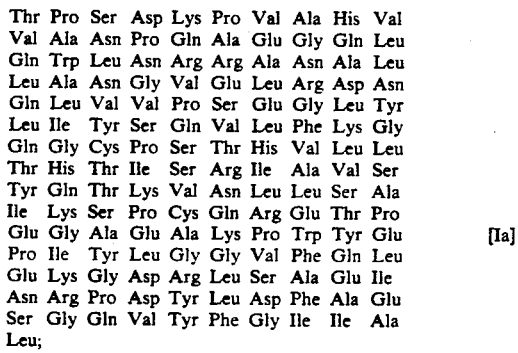

Thr Pro Ser Asp Lys Pro Val Ala His Val
Val Ala Asn Pro Gln Ala Glu Gly Gln Leu
Gln Trp Leu Asn Arg Arg Ala Asn Ala Leu
Leu Ala Asn Gly Val Glu Leu Arg Asp Asn
Gln Leu Val Val Pro Ser Glu Gly Leu Tyr
Leu Ile Tyr Ser Gln Val Leu Phe Lys Gly
Gln Gly Cys Pro Ser Thr His Val Leu Leu
Thr His Thr Ile Ser Arg Ile Ala Val Ser
Tyr Gln Thr Lys Val Asn Leu Leu Ser Ala
Ile Lys Ser Pro Cys Gln Arg Glu Thr Pro
Glu Gly Ala Glu Ala Lys Pro Trp Tyr Glu    [Ia]
Pro Ile Tyr Leu Gly Gly Val Phe Gln Leu
Glu Lys Gly Asp Arg Leu Ser Ala Glu Ile
Asn Arg Pro Asp Tyr Leu Asp Phe Ala Glu
Ser Gly Gln Val Tyr Phe Gly Ile Ile Ala
Leu;

and the formula [Ib] being as follows:

Ser-Ser-Ser-Arg          [Ib].

A preferred example of the polypeptide represented by X in formula III is a polypeptide represented by the following formula [Ic]:

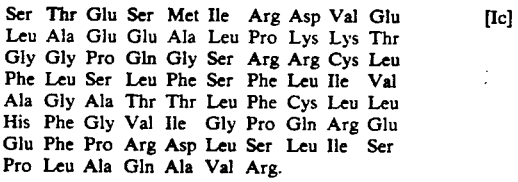

Ser Thr Glu Ser Met Ile Arg Asp Val Glu    [Ic]
Leu Ala Glu Glu Ala Leu Pro Lys Lys Thr
Gly Gly Pro Gln Gly Ser Arg Arg Cys Leu
Phe Leu Ser Leu Phe Ser Phe Leu Ile Val
Ala Gly Ala Thr Thr Leu Phe Cys Leu Leu
His Phe Gly Val Ile Gly Pro Gln Arg Glu
Glu Phe Pro Arg Asp Leu Ser Leu Ile Ser
Pro Leu Ala Gln Ala Val Arg.

Specific examples of the base sequences corresponding to the amino acid sequences represented by the above formulae [Ia], [Ib] and [Ic] are those represented respectively by the following formulae [IIa], [IIb] and [I-Ic].

(5')-ACC CCG AGT GAC AAG CCT GTA GCC
CAT GTT GTA GCA AAC CCT CAA GCT GAG GGG
CAG CTC CAG TGG CTG AAC CGC CGG GCC AAT
GCC CTC CTG GCC AAT GGC GTG GAG CTG AGA
GAT AAC CAG CTG GTG GTG CCA TCA GAG GGC
CTG TAC CTC ATC TAC TCC CAG GTC CTC TTC
AAG GGC CAA GGC TGC CCC TCC ACC CAT GTG
CTC CTC ACC CAC ACC ATC AGC CGC ATC GCC
GTC TCC TAC CAG ACC AAG GTC AAC CTC CTC [IIa]
TCT GCC ATC AAG AGC CCC TGC CAG AGG GAG
ACC CCA GAG GGG GCT GAG GCC AAG CCC TGG
TAT GAG CCC ATC TAT CTG GGA GGG GTC TTC
CAG CTG GAG AAG GGT GAC CGA CTC AGC GCT
GAG ATC AAT CGG CCC GAC TAT CTC GAC TTT
GCC GAG TCT GGG CAG GTC TAC TTT GGG ATC
ATT GCC CTG-(3')

(5')-TCA—TCT—TCT—CGA-(3')    [IIb]

(5')-AGC ACT GAA AGC ATG ATC CGG GAC    [IIc]
GTG GAG CTG GCC GAG GAG GCG CTC CCC AAG
AAG ACA GGG GGG CCC CAG GGC TCC AGG CGG
TGC TTG TTC CTC AGC CTC TTC TCC TTC CTG
ATC GTG GCA GGC GCC ACC ACG CTC TTC TGC
CTG CTG CAC TTT GGA GTG ATC GGC CCC CAG
AGG GAA GAG TTC CCC AGG GAC CTC TCT CTA
ATC AGC CCT CTG GCC CAG GCA GTC AGA-(3').

It should be understood that the DNAs in accordance with this invention include the following DNAS.

(1) DNAs encoding a human TNF polypeptide or its principal portion(s).

(2) DNAs being an allelic mutant of a DNA encoding a human TNF polypeptide or its principal portion(s).

(3) DNAs resulting from modification of DNAs encoding a human TNF polypeptide or its allelic mutant polypeptide.

(4) DNAs resulting from chemical or enzymatic modification of DNAs encoding a human TNF polypeptide or its allelic mutant polypeptide.

(5) Partially or fully chemically synthesized DNAs corresponding to DNAs encoding a human TNF polypeptide or its principal portion(s).

(6) DNAs encoding a polypeptide of which activity is essentially equivalent to that of a human TNF polypeptide or its principal portion(s).

(7) Any degenerative DNAs encoding a human TNF polypeptide or its principal portion(s).

(8) DNAs encoding a human TNF polypeptide in which one or more codons are deleted or replaced by other codon(s).

(9) DNAs encoding a human TNF polypeptide or its principal portion(s) and having an initiation codon and-/or termination codon and/or a promoter followed by Shine-Dalgarno sequence upstream of the initiation codon.

(10) DNAs containing a base sequence which differs from the base sequence encoding rabbit TNF but has high homology to a portion(s) of the base sequence encoding rabbit TNF.

Preferred DNAs in accordance with this invention are (1) DNA having a base sequence corresponding to an amino acid sequence represented by formula [I] in which A is formula [Ia], B is formula [Ib], X is formula [Ic], m and n are 1, and Y and p are the same as defined in formula [I];

(2) DNA having a base sequence corresponding to an amino acid sequence represented by formula [I] in which A is formula [Ia], B is formula [Ib], m is 1, n is 0, and Y and p are the same as defined in formula [I]; and (3) DNA having a base sequence corresponding to an amino acid sequence represented by formula [I] in which A is formula [Ia], m and n are 0 and Y and p are the same as defined in formula [I].

An especially preferred DNA is one having a base sequence corresponding to an amino acid sequence represented by formula [I] in which A is formula [Ia], B is formula [Ib], m is 1 or 0, and n and p are 0.

The base sequence corresponding to an amino acid sequence of formula [I] in which A is formula [Ia], B is formula [Ib]; X is formula [Ic], and m, n and p are each 1 is shown by the sequence of the bases Nos. 1 to 699 in Table 4 in which the bases are numbered. The base sequence corresponding to the amino acid sequence of formula [Ia] is shown by the sequence of the bases Nos. 247 to 699 in Table 4, and the total number of amino acids corresponding to this base sequence is 151.

In Table 4, the upper rows show the base sequence, and the lower rows, the corresponding amino acid sequence.

Examples of the polypeptide of formula [Ia] in which one or more amino acids are deleted or replaced include (4) a polypeptide of formula [Ia] in which Thr in the first position from the N-terminus has been deleted;

(5) a polypeptide of formula [Ia] in which the amino acid sequence from Thr in the 1st position to Pro in the 6th position from the N-terminus has been deleted;

(6) a polypeptide of formula [Ia] in which the amino acid sequence from Thr in the 1st position to His in 9th position from the N-terminus has been deleted;

(7) a polypeptide of formula [Ia] in which the amino acid sequence from Thr in the 1st position to Ala in the 2th position from the N-terminus has been deleted; and (8) a polypeptide of formula [Ia] in which the Thr and His in the 66th and 67th positions from the N-terminus have been replaced by His, Thr or Tyr.

The present inventors hold the view that at least
(9) a base sequence of the 577th to the 708th bases in the upper rows of Table 5, and especially
(10) a base sequence of the 658th to the 708th bases in the upper rows of Table 5
are important base sequences of DNA coding for a polypeptide having biological activity.

[I-3] Processes for the production of the DNAs of the invention will be described hereinbelow.

According to this invention, the DNA encoding a human TNF polypeptide or a principal portion thereof can be produced by cultivating human macrophages together with inducer(s), separating a fraction containing human TNF mRNA from the induced cells, preparing a cDNA library from the fraction, and cloning the human TNF cDNA by a differential hybridization method using a suitable prober for example a rabbit TNF cDNA fragment, or by a differential hybridization method followed by mRNA hybridization-translation assay.

In other words, it can be produced through the following steps.

A. Cultivating human macrophages with inducer(s),
B. separating a fraction containing human TNF mRNA from the induced cells,
C. preparing sscDNA from the mRNA by using reverse transcriptase and then converting it to dscDNA,
D. inserting the dscDNA into a vector, E. introducing the recombinant vector into a host to transform it and construct a cDNA (colony) library, and F. cloning cDNA encoding a human TNF polypeptide or its principal portion from the library.

If desired, modification (step G) of the DNA produced as above can give other DNAs of this invention which have or contain a base sequence corresponding to the amino acid sequence represented by formula (I).

Now, the processes for producing the DNA of this invention will be described in more detail. It should be understood however that the operations and conditions in the individual steps of the processes to be described hereinbelow are well known in the art, and the processes of this invention are never limited to these specific processes.

(1) Preparation of human TNF mRNA

The human TNF mRNA can be obtained from human macrophages, for example by the following method.

Human macrophages are obtained, for example, from human alveolus by the method of Sone, et all [J. Immunol., 129, 1313 (1982)], from blood by the method of Matthews [Br. J. Cancer, 48, 405 (1983)], from placenta by the method of Wilson, et al., [J. Immunological Methods, 56, 305 (1983)], or from other tissues.

The macrophages obtained thus are seeded in a dish at a cell density of about $2 \times 10^4$ to $1 \times 10^6$ cells per cm$^2$, and precultivated at 35° to 38° C., preferably about 37° C. in a fully humidified atmosphere containing 5% carbon dioxide for about 30 minutes to 2 hours.

Then, endotoxin obtained from a gram-negative bacterium, preferably lipopolysaccharide derived from *Escherichia coli, Pseudomonas aeruginosa* or *Salmonella typhi*, is added as an inducer, and cycloheximide is added as a protein synthesis inhibitor. The cultivation is continued further for 3 to 8 hours to accumulate human TNF mRNA in the macrophages. The pre-cultivation may be omitted. The amount of endotoxin is generally about 0.1 to 1000 micrograms/ml, preferably about 1 to 100 micrograms/ml. At this time, a phorbol ester such as phorbol-12-myristate-13-acetate, phorbol-12113-didecanoate or phorbol-12,13-dibenzoate may be further added as an inducer in an amount of about 1 to 2000 ng/ml. The amount of the protein synthesis inhibitor varies depending upon its type. For example, in the case of cycloheximider it is 0.1 to 50 micrograms/ml. Various culture media suitable for the cultivation of mammalian cells can be used as the culture medium. Examples include RPMI-1640, Eagle's MEM medium, and Dulbecco's modified MEM medium [for the compositions of the above media, see, for example, "Cell Cultivation Manual" edited by Y. Sohmura, Koaansha (1982), and J. Paul "Cell and Tissue Culture", E. & S. Livingstone Ltd. (1970)]. Preferably, an animal serum (such as fetal bovine serum or calf serum) is added to the culture medium in an amount of about 1 to 20%.

After the cultivation, total RNA is extracted from the cells by a customary method, for example the method of Chirgwin et al. [Biochemistry, 18, 5294 (1979)], and then by affinity column chromatography on oligo(dT)-cellulose or poly(U)Sepharose, or by a batch method, a fraction containing poly(A)mRNA is separated. An enriched mRNA fraction with human TNF mRNA can be obtained by subjecting the poly(A)mRNA fraction to acid-urea agarose gel electrophoresis or sucrose density gradient centrifugation.

To confirm that the resulting mRNA fraction is the desired one containing mRNA encoding human TNF polypeptide, the mRNA is translated into a protein and its biological activity is examined. This can be carried out, for example, by injecting the mRNA into the oocytes of *Xenopus laevis* or adding it to a suitable protein synthesizing system, such as a reticulocyte lysate or wheat germ cell-free protein synthesizing system and by confirming that the translated protein has cytotoxic activity on mouse L cells in vitro.

(2) Cloning of human TNF cDNA

The poly(A)mRNA or the enriched mRNA fraction obtained in step (1) above is used as a template and an oligo(dt) is used as a primer in order to synthesize sscDNA by using reverse transcriptase [for example, that derived from avian myeloblastosis virus (AMV)] in the presence of. dATP, dGTP, dCTP and dTTP. Then, the sscDNA is used as a template, and dscDNA is synthesized by using reverse transcriptase or *E. coli* DNA polymerase I (large fragment).

The resulting dscDNA is inserted, for example, into the restriction endonuclease Pst I cleavage site of plasmid pBR322 by a conventional method, for example the poly(dG)-poly(dC) homopolymer extension method [T. S. Nelson "Methods in Enzymology", 68, 41 (1979), Academic Press Inc,, New York]. The resulting recombinant plasmids are introduced into a host such as *E. coli* χ1776 in accordance with the method of Cohen et al. [Proc. Nat. Acad. Sci., U.S.A., 69, 2110 (1972)] to transform it, and by selecting tetracycline-resistant colonies, a cDNA (colony) library is prepared.

The cDNA library is subjected to colony hybridization [D. Hanahan et al., Gene, 10, 63 (1980)] by using a $^{32}$P-labelled rabbit TNF cDNA fragment obtained in Referential Example 1 as a probe, and the desired clones harboring recombinant plasmids containing a cDNA insert encoding human TNF polypeptide are screened.

If such a suitable TNF cDNA probe as shown above cannot be obtained, the desired clones are screened by colony hybridization using induction plus and minus probes, and by hybridization translation assay as follows.

A $^{32}$P-labelled cDNA is synthesized using the poly-(A)mRNA fraction or the enriched mRNA fraction containing the human TNF mRNA obtained in step (1) as a template and used as an induction plus probe. Separately, a mRNA fraction, obtained by the same procedure as above except that non-induced macrophages are used as a starting material, is used as a template and $^{32}$P-labelled cDNA is synthesized. The $^{32}$P-labelled cDNA is used as an induction minus probe. From the above cDNA library, plasmid clones which are strongly hybridized with the induction plus probe but not hybridized with the induction minus probe are selected.

The following method is carried out in order to confirm that the resulting clones harbor a cDNA insert encoding human TNF polypeptide. The plasmid DNAs are isolated from the above clones, converted to a single-stranded DNA by heating or alkali treatment, and fixed onto nitrocellulose filters. The mRNA fraction containing human TNF mRNA is added to the filters to hybridize with the fixed DNA. Then, the hybridized mRNA is eluted and recovered. The recovered mRNA is injected into the oocytes of *Xenopus laevis* to determine whether the recovered mRNA encodes human TNF polypeptide.

The above methods give transformants harboring a recombinant plasmid having a DNA fragment containing a base sequence complementary to the human TNF mRNA.

When the obtained cloned cDNAs do not contain the whole coding region of human TNF polypeptide, cDNAs of a larger size are selected by screening the cDNA library using as a probe the cloned TNF cDNA fragments from the transformants selected as above.

The cloned cDNA encoding a polypeptide containing the amino acid sequence of human TNF polypeptide can be proved finally by analyzing the base sequences of some the resulting cloned cDNA fragments in accordance with, for example, the Maxam-Gilbert method [Proc. Nat, Acad. Sci., U.S.A., 74, 560 (1977)] searching for base sequence which have a homology with the base sequence of rabbit TNF cDNA, and selecting cDNAs containing a base sequence corresponding to the whole coding region of human TNF polypeptide.

Homology between the base sequence coding for rabbit TNF and that coding for human TNF polypeptide, and homology between the deduced amino acid sequences of rabbit TNF and human TNF polypeptide are shown in Tables 5 and 6, respectively.

By judging from these homologies and the determined N-terminal and C-terminal amino acid sequences of rabbit plasma TNF (see Referential Example 3 below), it is found that human TNF cDNA codes for its precursor polypeptide of 233 amino acid residues and a mature human TNF polypeptide is a polypeptide corresponding to the 155 amino acid residues from the carboxy-terminus of its precursor.

The mature human TNF polypeptide is coded in the base sequence corresponding to an amino acid sequence represented by formula [I] in which A is formula [Ia], B is formula [Ib], m is 1, and n and p are 0.

The human TNF precursor polypeptide is coded in the base sequence corresponding to an amino acid sequence represented by formula [I] in which A is formula [Ia], B is formula [Ib], X is formula [Ic], and m, n and p are 1, and Y is Met.

High homologies in the base sequences and the deduced amino acid sequences as above may indicate that the human and rabbit TNFs are phylogenetically derived from the same gene, And suggest that a considerable portion(s) of the common regions are a sequence necessary for expressing their biological activities. However, mature human TNF polypeptide did not cross immunologically with rabbit plasma TNF as shown below. It is indicated that the whole amino acid sequence of mature human TNF polypeptide is not always necessary for expressing the activities, and that a partially modified human TNF polypeptide also has the activities so long as it contains an active site of the mature TNF polypeptide.

(3) Modification of the DNA encoding human TNF polypeptide

The DNA encoding the human TNF polypeptide can be modified by techniques known per se to form DNAs having or containing a base sequence corresponding to the amino acid sequence represented by formula [I]. Modification is carried out, for example, by cleaving the DNA with suitable restriction endonuclease(s) and splitting off one or more codons with suitable exonucleases and/or endonucleases singly or in combinations followed by replacing with degenerative or other codons, for example, those synthesized chemically by the phosphotriester method [Ohtsuka, E., et al., Heterocycles, 15, 395 (1981)], or by ligating without any supplement of codons to prepare DNA having one or more codons deleted.

[II-1] The present invention, as stated above, also relates to a polypeptide having or containing a human tumor necrosis factor polypeptide or its principal portion(s), a human tumor necrosis factor-like substance, its principal portion(s) and their chemically or enzymatically modified substances. They are more specifically a polypeptide of the following formula II].

$$(Y)_p-(X)_n-(B)_m-A \qquad [I]$$

or its derivative or a salt thereof, wherein
A is a polypeptide of the formula [Ia] below in which one or more amino acids may be deleted or replaced by other amino acid(s),
B is a peptide of the formula [Ib] below in which one to three amino acids may be deleted or replaced by other amino acid(s),
X is a polypeptide,
Y is Met, and
m, n and p are 1 or 0;
the formula [Ia] being as follows:

Thr Pro Ser Asp Lys Pro Val Ala His Val
Val Ala Asn Pro Gln Ala Glu Gly Gln Leu
Gln Trp Leu Asn Arg Arg Ala Asn Ala Leu
Leu Ala Asn Gly Val Glu Leu Arg Asp Asn
Gln Leu Val Val Pro Ser Glu Gly Leu Tyr
Leu Ile Tyr Ser Gln Val Leu Phe Lys Gly
Gln Gly Cys Pro Ser Thr His Val Leu Leu
Thr His Thr Ile Ser Arg Ile Ala Val Ser
Tyr Gln Thr Lys Val Asn Leu Leu Ser Ala
Ile Lys Ser Pro Cys Gln Arg Glu Thr Pro
Glu Gly Ala Glu Ala Lys Pro Trp Tyr Glu       [Ia]
Pro Ile Tyr Leu Gly Gly Val Phe Gln Leu
Glu Lys Gly Asp Arg Leu Ser Ala Glu Ile
Asn Arg Pro Asp Tyr Leu Asp Phe Ala Glu
Ser Gly Gln Val Tyr Phe Gly Ile Ile Ala
Leu;

and the formula [Ib] being as follows:

Ser-Ser-Ser-Arg                                [Ib].

A preferred example of the polypeptide represented by X in formula [I] is a polypeptide represented by the following formula [Ic].

Ser Thr Glu Ser Met Ile Arg Asp Val Glu      [Ic]
Leu Ala Glu Glu Ala Leu Pro Lys Lys Thr
Gly Gly Pro Gln Gly Ser Arg Arg Cys Leu
Phe Leu Ser Leu Phe Ser Phe Leu Ile Val
Ala Gly Ala Thr Thr Leu Phe Cys Leu Leu
His Phe Gly Val Ile Gly Pro Gln Arg Glu
Glu Phe Pro Arg Asp Leu Ser Leu Ile Ser
Pro Leu Ala Gln Ala Val Arg.

It should be understood that the polypeptides in accordance with this invention include the following polypeptides.

(1) A polypeptide corresponding to the DNA of this invention described in section [I] above which is produced by host transformed with an expression vector having the aforesaid DNA inserted thereinto;
(2) a human TNF polypeptide or its precursor polypeptide;

(3) a human TNF polypeptide in which one or more amino acids are deleted or replaced by other amino acid(s);

(4) a polypeptide consisting of a principal portion of the human TNF polypeptide;

(5) a polypeptide which differs from rabbit TNF polypeptide but contains or has a peptide having high homology to a portion(s) of rabbit TNF polypeptide;

(6) a degraded product of the human TNF polypeptide degradated in a host;

(7) a polypeptide resulting from chemical or enzymatic modification of the human TNF polypeptide, or its derivative; and (8) a polypeptide possessing or potentially possessing biological activities substantially equivalent to those of the human TNF polypeptide.

Preferred polypeptides in accordance with this invention are as follows:

(1) A polypeptide of formula [I] in which A is formula [Ia], B is formula [Ib], m is 1, n is 0, and Y and p are the same as defined in formula [I], (2) a polypeptide of formula [I] in which A is formula [Ia], m and n are 0 and Y and p are the same as defined in formula [II, and (3) a polypeptide of formula [I] in which A is formula [Ia], B is formula [Ib], X is formula [Ic], m and n are 1, and Y and p are the same as defined in formula [I].

An especially preferred polypeptide is a polypeptide of formula [I] in which A is formula [Ia], B is formula [Ib], m is 1 or 0. and n and p are of or its physiologically acceptable salts.

The polypeptide of formula [Ia] is a polypeptide having the amino acid sequence from the 86th to 236th bases in the upper rows of Table 6.

Polypeptides of formula [Ia] in which one or more amino acids have been deleted or replaced include, for example, the following polypeptides.

(4) A polypeptide of formula [Ia] in which Thr in the 1st position from the N-terminus has been deleted;

(5) a polypeptide of formula [Ia] in which the amino acid sequence from Thr in the 1st position to Pro in the 6th position from the N-terminus has been deleted;

(6) a polypeptide of formula [Ia] in which the amino acid sequence from Thr in the 1st position to His in the 9th position from the N-terminus has been deleted;

(7) a polypeptide of formula [Ia] in which the amino acid sequence from Thr in the 1st position to Ala in the 12th position from the N-terminus has been deleted; and (8) a polypeptide of formula [Ia] in which the Thr and His in the 66th and 67th positions from the N-terminus have been replaced by His, Thr or Tyr.

The present inventors hold the view that at least (9) an amino acid sequence from Trp in the 193rd position to Leu in the 236th position in the upper rows of Table 6, and especially

(10) an amino acid sequence from Tyr in the 220th position to Leu in the 236th position in the upper rows of Table 6 are important amino acid sequences of a polypeptide having biological activity.

The derivatives of the polypeptides of formula [I] may, for example, be those formed by utilizing the side chain functional groups on the chain of the polypeptide of formula [I], the amino group at the N-terminus, or the carboxyl group at the C-terminus, such as an ester formed between the carboxyl group and an aliphatic alcohol, an acid amide formed between the primary or secondary amine with an acid or its derivative, or an O-acyl derivative of the hydroxyl group.

The salts of the polypeptides [I] are salts formed with the carboxyl or amino group of the polypeptides [I], for example salts formed with sodium hydroxide, potassium hydroxide, arginine, caffeine, procaine, hydrochloric acid, and gluconic acid.

The polypeptides [I] may exist as their aggregates, such as a trimer, and such aggregates are naturally included within the polypeptides of this invention.

[II-2] Processes for the production of the polypeptides of this invention will be described hereinbelow.

According to this invention, a polypeptide having or containing a human TNF polypeptide or a principal portion thereof can be produced by the following steps.

A. Inserting the DNA having or containing a base sequence encoding human TNF polypeptide or its principal portion, or its modified base sequence into an expression vector, B. introducing the recombinant vector into a host, C. cultivating the host transformed with the recombinant vector to produce the polypeptide, D. collecting the cultured cells and extracting the polypeptide produced from them#and E. purifying the polypeptide by conventional purifying methods for proteins.

If desired, the polypeptide produced through the above steps may be modified (step F) to produce other polypeptides of this invention represented by formula [I], or their derivatives or salts.

(1) Production of human TNF polypeptide

A detailed description will follow of the processes for producing the human TNF polypeptide by using the DNA of this invention.

An expression vector for production of human TNF polypeptide can be obtained by inserting the cloned cDNA encoding human TNF polypeptide into a suitable vector. All vectors which proliferate in microorganisms to be transformed can be used. Examples include plasmids (such as *E. coli* plasmid pBR322), phages (such as phage derivatives), and viruses (such as SV40). They may be used singly or in combination, for example as a pBR322-SV40 hybrid plasmid. The site of insertion of the DNA can be properly selected. In other words, a suitable site of a suitable vector may be cleaved with a suitable restriction endonuclease in a customary manner, and the cloned cDNA of a suitable length may be inserted into the cleavage site.

More specifically, an expression vector for production of the non-fused polypeptide is constructed by joining a DNA fragment containing the base sequence encoding the human TNF polypeptide in which the initiation codon ATG is added to the 5'-terminus and the termination codon (TAA, TAG or TGA) exists at the 3'-terminus, to a DNA fragment with a suitable promoter and the Shine-Dalgarno sequence and inserting it into a vector. An expression vector for the production of the fused polypeptide may be constructed by inserting the cDNA fragment having the base sequence encoding the human TNF polypeptide in which the termination codon is added to the 3'-terminus into the vector so that the translational reading frame coincides with that of the structure gene to be fused. The process for the production of human TNF polypeptide as a fused polypeptide has the advantage of minimizing degradation of the product in the transformed host cells. In this case, human TNF polypeptide should be cut out from the fused product. Mature human TNF polypeptide corresponding to an amino acid sequence from Ser in the 82nd position to Leu in the 236th position in the upper rows of Table 6 does not contain any methionine as a component. Therefore, by using an expression vector constructed by inserting the human TNF cDNA fragment ligated with the 3'-terminus of the base sequence of a structure gene to be fused through a methionine codon (ATG), the human TNF polypeptide is easily obtained from the fused product by a method of cleavage of methionyl peptide bond, for example, by a cyanogen bromide treatment [Itakurat K., et al., Science 198, 1054 (1977)].

Examples of the promoters are lac, trp, tac, phoS, phoA, PL and SV40 early promoters.

Transformants are obtained by introducing the expression vector into a host such as microorganism, animal or plant cells. For example, E. coli is transformed by the method of Cohen et al. [Proc. Nat. Acad. Sci., USA, 69, 2110 (1972)]. Then, by cultivating one of the transformants, a human TNF polypeptide or the polypeptide with a methionine at its N-terminus is produced. The product can be accumulated either in the cytoplasm or in the periplasm of the host cells depending upon the method of constructing the expression vector. To cause the polypeptide to be secreted in the periplasm, one can construct an expression vector by using a gene coding for a secretory protein, such as an alkaline phosphatase gene (phoA) or a phosphate binding protein gene (phoS), and joining DNA encoding the human TNF polypeptide in the correct translational reading frame to the above gene at a suitable site following a DNA region encoding the signal peptide.

The resulting transformants are cultivated under suitable conditions for the transformants until the polypeptide desired is fully produced. Then, the polypeptide is extracted from the culture. When the produced polypeptide is accumulated in the cytoplasm, the host cells are destroyed by lysozyme digestion and freezing and thawing or sonication or by using a French press, and then centrifuged or filtered to collect the extract. When it is accumulated in the periplasm, it can be extracted, for example, by the method of Willsky et al. [J. Bacteriol., 127, 595 (1976)].

The crude polypeptide so obtained can be purified by conventional purifying methods for proteins, for example by combinations of salting out, ultrafiltration, dialysis, ion exchange chromatography, gel filtration, electrophoresis, affinity chromatography, etc.

By the foregoing process, the human TNF polypeptide of the invention and/or the polypeptide with a methionine at the N-terminus of the polypeptide can be produced.

Polypeptides in accordance with this invention other than the human TNF polypeptide and the polypeptide with a methionine at the N-terminus of the polypeptide can also be produced by using the desired DNA substantially in accordance with the above process, or by using proper combinations of known processes.

(2) Modification of human TNF polypeptide

The modified human TNF polypeptides mean polypeptides derived from the allelic mutants of the DNA encoding human TNF polypeptide (allelic mutant polypeptide), a polypeptide resulting from addition of an amino acid or peptide (consisting of two or more amino acids) to the N-terminus or C-terminus of the human TNF polypeptide or the allelic mutant polypeptide, a polypeptide resulting from deletion of one or more amino acids from the human TNF polypeptide or the allelic mutant-polypeptide (for example, deletion of 4 amino acids from the N-terminus of human TNF polypeptide as shown in Section III-1, (6) below), derivatives such as esters, acyl-derivatives or acid amides, formed by using a functional group in the molecule, an amino residue of N-terminus or a carboxy residue of the C-terminus, and its salt formed by using amino residues or carboxy residues with, for example, sodium hydroxide, potassium hydroxide, arginine, caffeine, procaine, hydrochloric acid, gluconic acid and so on.

Modification of the human TNF polypeptide or its allelic mutant polypeptide is carried out by techniques known per se, which are published in, for example, "Chemical Modification of Proteins, by Means, G. E. and Feeney, R. E., Holden-Day, Inc. California (1971)", to produce the modified human TNF polypeptide as mentioned above.

[III] The chemical and physicochemical properties, biological activities and immunological property of the typical polypeptides of this invention will be described below in detail.

Purified human TNF polypeptide obtained in Example 4 (to be referred to as recombinant human TNF, abbreviated to rHu-TNF) was used for analysis as shown below.

[III-1] Chemical and physicochemical properties (1) Molecular weight

The molecular weight of rHu-TNF was measured by gel filtration analysis with TSK-gel G3000 SW column (7.5×600 mm, Toyo Soda) in accordance with high-performance liquid chromatography using 0.2M phosphate (pH 7) buffer with and without 8M urea and 0.5% 2-mercaptoethanol as a solvent. As molecular weight marker proteins, the following proteins were used: bovine serum albumin: (MW: $6.6 \times 10^4$), rabbit triosephosphate isomerase (MW: $5.3 \times 10^4$), ovalbumin (MW: $4.5 \times 10^4$), porcine pepsin (MW: $3.27 \times 10^4$), soybean trypsin inhibitor (MW: $2.05 \times 10^4$), horse myoglobin (MW: $1.78 \times 10^4$), and horse cytochrome c (MW: $1.24 \times 10^4$).

As a result, rHu-TNF had a molecular weight of 45,000±5,000 daltons and 18,000±3,000 daltons in the absence and presence of urea and 2-mercaptoethanol, respectively.

The cDNA inserted into the expression plasmid pHTR91 encoded 155 amino acid residues (omitting a methionine derived from an initiation codon ATG). The theoristical molecular weight of rHu-TNF was calculated as 17,097 daltons from the amino acid sequence deduced. The calculated molecular weight agreed with the value determined in the presence of urea and 2-mercaptoethanol.

This finding indicates that rHu-TNF occurs as a monomer (subunit) in the presence of urea and 2-mercaptoethanol, but exists as an aggregate, for example a trimer in the absence of denaturants.

(2) Isoelectric Point

The isoelectric point was determined by isoelectrofocusing gel electrophoresis at 3 watt for 3 hours using a 5% polyacrylamide flat gel with a pH gradient ranging from pH 4.0 to pH 6.5 created with Pharmalyte (Pharmacia).

Protein was stained with Coomassie brilliant blue. Separately, the gel was sliced into 3 mm width and immersed in 20 mM Tris-HCl (pH 7.8) buffer to elute a protein. Cytotoxic activity was obviously detected in an elute from the gel sliced from the position corresponding to the position of a protein detected by the staining.

Isoelectric point of rHu-TNF was found to be 5.9±0.3.

(3) Amino acid composition

The amino acid composition of rHu-TNF was determined with a micro-amino acid analyzer (Shimadzu Seisakusho) by a fluorometric method using orthophthalaldehyde after the sample was hydrolyzed with hydrochloric acid.

Fifty micrograms of rHu-TNF was hydrolyzed in 6N HCl at 110° C. The contents of the amino acids were calculated by correcting on the basis of the values determined with each sample hydrolyzed for 24, 48 and 72 hours. Cystine (or cysteine) was determined as a cysteic acid converted by performic acid oxidation. Tryptophan was determined by a fluorometric method of Pajot [Eur. J. Biochem., 63, 263 (1976)].

The results are summarized in Table 7.

The amino acid composition well agreed with that deduced from the base sequence encoding human TNF polypeptide.

(4) Determination of N-terminal amino acid sequence

The N-terminal amino acid sequence of rHu-TNF was determined by the Edman degradation method [Arch. Biochem. Biophys., 22, 475 (1949)].

A phenylthiohydantoin-amino acid derived from a N-terminal amino acid by the Edman degradation method was identified by high-performance liquid chromatography using a column (4.6×250 mm) of TSK-gel ODS-120A (Toyo Soda). These procedures were serially repeated to determine a newly formed N-terminal amino acid sequentially.

It was consequently found that the N-terminal amino acid sequence of rHu-TNF was as follows:

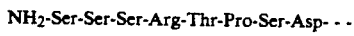

NH$_2$-Ser-Ser-Ser-Arg-Thr-Pro-Ser-Asp- - -

It has been known that some polypeptides produced in microorganisms by application of the recombinant DNA technology have a methionine residue derived from an initiation codon (ATG) at its N-terminus. However, in the case of rHu-TNF obtained in Example 5, a methionine residue could not be detected at the N-terminus and was completely removed off.

(5) Determination of C-terminal amino acid sequence

The C-terminal amino acid sequence of rHu-TNF was determined by the enzymatic method using carboxypeptidases.

The rHu-TNF was digested with carboxypeptidase-A and carboxypeptidase-Y at the molar ratios of enzyme to substrate of 1:25 and 1:1,000, respectively. The free amino acids released from the C-terminus of rHu-TNF by the double digestion were identified by a micro-amino acid anayzer (Shimadzu Seisakusho) at appropriate intervals from 2 minutes to 180 minutes after the digestion.

It was consequently found that the C-terminal amino acid sequence of rHu-TNF was as follows:

- - -Tyr-Phe-Gly-Ile-Ile-Ala-Leu-COOH

(6) Trypsin digestion of rHu-TNF

Five hundred micrograms of rHu-TNF was digested with 20 micrograms of TPCK-treated trypsin (type XIII, SIGMA Chemical Co.) in 5 mM Tris-HCl (pH 7.8) buffer at room temperature for 5 hours. The digested product was subjected to a preparative isoelectrofocusing gel electrophoresis as shown in Example 4-(2). The proteins were stained with Coomassie brilliant blue. Separately, the gel was sliced into 3 mm width and the sliced gels were immersed in 20 mM Tris-HCl (pH 7.8) buffer to elute a protein.

As a result, the digested product eluted from the sliced gel corresponding to the pH zone being about 0.3 lower than the isoelectric point of rHu-TNF had cytotoxic activity.

The digested product with cytotoxic activity was subjected to determination of the N-terminal and C-terminal amino acid sequences by the methods as described in sections (5) and (6), respectively.

Consequently, the partial amino acid sequence of the digested product were as follows:

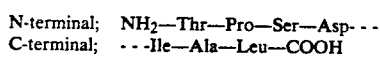

N-terminal; NH$_2$—Thr—Pro—Ser—Asp- - -
C-terminal; - - -Ile—Ala—Leu—COOH

By judging from the amino acid sequence, the digested product is a polypeptide resulting from splitting off of the four N-terminal amino acids (Ser-Ser-Ser-Arg) from the rHu-TNF, and has a cytotoxic activity as mentioned above. It means that at least four amino acids at the N-terminus of rHu-TNF are not essential to its biological activity.

[III-2] Biological activities

(1) Cytotoxic activity against mouse L-M cell

The method of measuring the cytotoxic activity against mouse L-M cell (ATCC, CCL 1.2) was as follows:

A sample (0.1 ml) diluted serially with the below-mentioned medium and 0.1 ml of a mouse L-M cell suspension (1×10$^5$ cells/ml) were added to each well of a 96 well multi-well plate (Flow Labs.). The Eagle's minimum essential medium [see, for example, J. Paule "Cell and Tissue Culture", E & S. Livingstone Ltd. (1970)] containing 1% fetal bovine serum was used. The plate was incubated at 37° C. for 48 hours in a fully humidified atmosphere containing 5% carbon dioxide. After incubation, 20 microliters of 25% glutaraldehyde was added to fix the viable cells. After fixation, the plate was washed and dried. Then, 0.1 ml of 0.05% methylene blue solution was added to stain the fixed cells. The excess of methylene blue was washed off, and the plate was dried. Methylene blue associated with the fixed cells was eluted with 200 microliters of 0.36N HCl and its absorbance at 665 nm was measured with a Titertek Multiscan (Flow Labs.). The absorbance is proportional to the number of the viable cells. The concentration of biological activity required to kill 50% of the L-M cells was defined as one unit/ml. The cytotoxic acitivity against mouse L-M cells determined under the conditions as above was represented by "units (LM)", to distinguish from the cytotoxic activity against mouse L-929 cells as a target cell.

The protein content was determined by the method of Lowry, O. H., et al. [J. Bio. Chem., 193, 265 (1951)].

As a result the rHu-TNF had a specific activity of $2 \times 10^6$ units (LM) or more per mg of protein.

(2) Antitumor effect on Meth A sarcoma transplanted into mice

The antitumor effect on mice bearing Meth A sarcoma was evaluated by the following method.

BALB/C mice weighing about 23 g were intradermally transplanted with $2 \times 10^5$ Meth A sarcoma cells into the abdominal skin, and seven days later, mice were selected whose tumor was 6–7 mm in diameter. On the 7th day after the tumor transplantation, the rHu-TNF was administered into the tumor mass or intravenously. Endotoxin content of the rHu-TNF preparation was less than 0.01 ng per $1 \times 10^4$ units (LM) of its cytotoxic activity.

As a result, by administration into the tumor mass, a necrotic response in the tumor transplant was observed in all mice injected with rHu-TNF at a dose of $1 \times 10^3$, $3 \times 10^3$ and $1 \times 10^4$ units (LM) per mouse within 24 hours after the injection, and the tumor was completely regressed at a ratio of 3/5, 5/5 and 5/5 at each dose as shown above, respectively. By intravenous administration, a necrotic response was observed in all mice injected with rHu-TNF at a dose of $3 \times 10^3$ and $1 \times 10^4$ units (LM) per mouse, and the ratio of complete regression was 3/5 and 4/5, respectively.

(3) Inhibitory effect of rHu-TNF on the growth of human tumor cells in vitro

The inhibitory effect of rHu-TNF on the growth of human tumor cells and normal cells was evaluated in vitro under the following conditions. Human tumor cells or normal cells were seeded at $1 \times 10^4$ cells per well in 1 ml of Eagle's minimum essential medium containing 10% fetal bovine serum using a 24 well multi-well plate. rHu-TNF was added at a final concentration of 100 units (LM)/ml and then cultivated at 37° C. for 4 days in a fully humidified atmosphere containing 5% carbon dioxide. Four hours before the termination of cultivation, 1 microcurie of $^3$H-thymidine was added into each well. After cultivation, the cells were washed with phosphate buffered saline, and lysed with 0.5% sodium dodecylsulfate. The amount of $^3$H-thymidine incorporated into the cells was determined by counting the radioactivity in the lysate.

The inhibitory effect was represented by a ratio of the growth inhibition calculated by the following equation:

Ratio of growth inhibition $(\%) = (a-b)/a \times 100$ wherein, a and b are the radioactivities incorporated into the cells in the absence of rHu-TNF and in the presence of rHu-TNF, respectively.

The results summarized in Table 8 show that rHu-TNF significantly inhibited the growth of human tumor cells, but did not affect normal cells. This finding indicates that rHu-TNF attacks tumor cells selectively.

[III-3] Immunological property

The rHu-TNF solution [100 units (LM)/ml] was mixed with an equal volume of a 100-fold dilution of the purified anti-rabbit plasma TNF antibody obtained in Referential Example 4. After incubation at 37 0C for 2 hours, the cytotoxic activity of the reaction mixture was measured by the method as described above using L-M cells as a target cell.

As a result, the cytotoxic activity of rHu-TNF was not neutralized with the antibody at all. It was found therefore that human TNF polypeptide was immunologically distinguishable from rabbit TNF.

[IV] For formulating the polypeptides of this invention, they may be in the form of a solution or a lyophilized product. From the standpoint of long-term stability, they are desirably in the form of lyophilized products. It is preferred to add vehicles or stabilizers to the preparations. Examples of the stabilizers include albumin, globulin, gelatin, protamine, protamine salts, glucose, galactose, xylose, mannitol, glucuronic acid, trehalose, dextran, hydroxyethyl starch, and nonionic surface-active agents (such as polyoxyethylene fatty acid esters, polyoxyethylene alkyl ethers, polyoxyethylene alkyl phenyl ethers, polyoxyethylene sorbitan fatty acid esters, polyoxyethylene glycerin fatty acid esters, polyoxyethylene hardened castor oil, polyoxyethyene castor oil, polyoxyethylene polyoxypropylene alkyl ethers, polyoxyethylene polyoxypropylene block copolymer, sorbitan fatty acid esters, sucrose fatty acid esters and glycerin fatty acid esters).

[V] The polypeptides of this invention are useful as antitumor agents because they have a selective cytotoxic effect on tumor cells and regress tumors of tumor-bearing animals.

Such polypeptide preparations are preferably administered parenterally or topically. Parenteral routes such as intraveous and intramuscular routes are used when tumor cells extend over a wide range or metastasize, or when prevention of metastasis is intended. Against local tumor tissues, direct intratumor administration is preferred. The dosage varies depending upon the type and size of tumors, the condition of the patient and the route of administration. Usually, it is $1 \times 10^2$ to $1 \times 10^7$ units (LM)/kg, preferably $1 \times 10^3$ to $1 \times 10^6$ units (LM)/kg.

TABLE 1-1

[1-1]

| (5')-TCA | GCT | TCT | CGG | GCC | CTG | AGT | GAC | AAG |
|---|---|---|---|---|---|---|---|---|
| CCT | CTA | GCC | CAC | GTA | GTA | GCA | AAC | CCG | CAA |
| GTG | GAG | GGC | CAG | CTC | CAG | TGG | CTG | AGC | CAG |
| CGT | GCG | AAC | GCC | CTG | CTG | GCC | AAC | GGC | ATG |
| AAG | CTC | ACG | GAC | AAC | CAG | CTG | GTG | GTG | CCG |
| GCC | GAC | GGG | CTG | TAC | CTC | ATC | TAC | TCC | CAG |
| GTT | CTC | TTC | AGC | GGT | CAA | GGC | TGC | CGC | TCC |
| TAC | GTG | CTC | CTC | ACT | CAC | ACT | GTC | AGC | CGC |
| TTC | GCC | GTC | TCC | TAC | CCG | AAC | AAG | GTC | AAC |
| CTC | CTC | TCT | GCC | ATC | AAG | AGC | CCC | TGC | CAC |
| CGG | GAG | ACC | CCC | GAG | GAG | GCT | GAG | CCC | ATG |
| GCC | TGG | TAC | GAG | CCC | ATC | TAC | CTG | GGC | GGC |
| GTC | TTC | CAG | TTG | GAG | AAG | GGT | GAC | CGG | CTC |
| AGC | ACC | GAG | GTC | AAC | CAG | CCT | GAG | TAC | CTG |
| GAC | CTT | GCC | GAG | TCC | GGG | CAG | GTC | TAC | TTT |

TABLE 1-1-continued

| | | | | |
|---|---|---|---|---|
| GGG | ATC | ATT | GCC | CTG-(3') |

TABLE 1-2

[1-2]

| | | | | | | | | | |
|---|---|---|---|---|---|---|---|---|---|
| Ser | Ala | Ser | Arg | Ala | Leu | Ser | Asp | Lys | Pro |
| Leu | Ala | His | Val | Val | Ala | Asn | Pro | Gln | Val |
| Glu | Gly | Gln | Leu | Gln | Trp | Leu | Ser | Gln | Arg |
| Ala | Asn | Ala | Leu | Leu | Ala | Asn | Gly | Met | Lys |
| Leu | Thr | Asp | Asn | Gln | Leu | Val | Val | Pro | Ala |
| Asp | Gly | Leu | Tyr | Leu | Ile | Tyr | Ser | Gln | Val |
| Leu | Phe | Ser | Gly | Gln | Gly | Cys | Arg | Ser | Tyr |
| Val | Leu | Leu | Thr | His | Thr | Val | Ser | Arg | Phe |
| Ala | Val | Ser | Tyr | Pro | Asn | Lys | Val | Asn | Leu |
| Leu | Ser | Ala | Ile | Lys | Ser | Pro | Cys | His | Arg |
| Glu | Thr | Pro | Glu | Glu | Ala | Glu | Pro | Met | Ala |
| Trp | Tyr | Glu | Pro | Ile | Tyr | Leu | Gly | Gly | Val |
| Phe | Gln | Leu | Glu | Lys | Gly | Asp | Arg | Leu | Ser |
| Thr | Glu | Val | Asn | Gln | Pro | Glu | Tyr | Leu | Asp |
| Leu | Ala | Glu | Ser | Gly | Gln | Val | Tyr | Phe | Gly |
| Ile | Ile | Ala | Leu | | | | | | |

TABLE 2-1

| | | | | | | | | |
|---|---|---|---|---|---|---|---|---|
| (5')-AGC | ACT | GAG | AGT | ATG | ATC | CGG | GAC | GTC |
| GAG | CTG | GCG | GAG | GGG | CCG | CTC | CCC | AAG | AAG |
| GCA | GGG | GGG | CCC | CAG | GGC | TCC | AAG | CGC | TGC |
| CTC | TGC | CTC | AGC | CTC | TTC | TCT | TTC | CTG | CTC |
| GTG | GCT | GGA | GCC | ACC | ACG | CTC | TTC | TGC | CTG |
| CTG | CAC | TTC | AGG | GTG | ATC | GGC | CCT | CAG | GAG |
| GAA | GAG | CAG | TCC | CCA | AAC | AAC | CTC | CAT | CTA |
| GTC | AAC | CCT | GTG | GCC | CAG | ATG | GTC | ACC | CTC |
| AGA | TCA | GCT | TCT | CGG | GCC | CTG | AGT | GAC | AAG |
| CCT | CTA | GCC | CAC | GTA | GTA | GCA | AAC | CCG | CAA |
| GTG | GAG | GGC | CAG | CTC | CAG | TGG | CTG | AGC | CAG |
| CGT | GCG | AAC | GCC | CTG | CTG | GCC | AAC | GGC | ATG |
| AAG | CTC | ACG | GAC | AAC | CAG | CTG | GTG | GTG | CCG |
| GCC | GAC | GGG | CTG | TAC | CTC | ATC | TAC | TCC | CAG |
| GTT | CTC | TTC | AGC | GGT | CAA | GGC | TGC | CGC | TCC |
| TAC | GTG | CTC | CTC | ACT | CAC | ACT | GTC | AGC | CGC |
| TTC | GCC | GTC | TCC | TAC | CCG | AAC | AAG | GTC | AAC |
| CTC | CTC | TCT | GCC | ATC | AAG | AGC | CCC | TGC | CAC |
| CGG | GAG | ACC | CCC | GAG | GAG | GCT | GAG | CCC | ATG |
| GCC | TGG | TAC | GAG | CCC | ATC | TAC | CTG | GGC | GGC |
| GTC | TTC | CAG | TTG | GAG | AAG | GGT | GAC | CGG | CTC |
| AGC | ACC | GAG | GTC | AAC | CAG | CCT | GAG | TAC | CTG |
| GAC | CTT | GCC | GAG | TCC | GGG | CAG | GTC | TAC | TTT |
| GGG | ATC | ATT | GCC | CTG-(3') | | | | | |

TABLE 2-2

[2-2]

| | | | | | | | | | |
|---|---|---|---|---|---|---|---|---|---|
| Ser | Thr | Glu | Ser | Met | Ile | Arg | Asp | Val | Glu |
| Leu | Ala | Glu | Gly | Pro | Leu | Pro | Lys | Lys | Ala |
| Gly | Gly | Pro | Gln | Gly | Ser | Lys | Arg | Cys | Leu |
| Cys | Leu | Ser | Leu | Phe | Ser | Phe | Leu | Leu | Val |
| Ala | Gly | Ala | Thr | Thr | Leu | Phe | Cys | Leu | Leu |
| His | Phe | Arg | Val | Ile | Gly | Pro | Gln | Glu | Glu |
| Glu | Gln | Ser | Pro | Asn | Asn | Leu | His | Leu | Val |
| Asn | Pro | Val | Ala | Gln | Met | Val | Thr | Leu | Arg |
| Ser | Ala | Ser | Arg | Ala | Leu | Ser | Asp | Lys | Pro |
| Leu | Ala | His | Val | Val | Ala | Asn | Pro | Gln | Val |
| Glu | Gly | Gln | Leu | Gln | Trp | Leu | Ser | Gln | Arg |
| Ala | Asn | Ala | Leu | Leu | Ala | Asn | Gly | Met | Lys |
| Leu | Thr | Asp | Asn | Gln | Leu | Val | Val | Pro | Ala |
| Asp | Gly | Leu | Tyr | Leu | Ile | Tyr | Ser | Gln | Val |
| Leu | Phe | Ser | Gly | Gln | Gly | Cys | Arg | Ser | Tyr |
| Val | Leu | Leu | Thr | His | Thr | Val | Ser | Arg | Phe |
| Ala | Val | Ser | Tyr | Pro | Asn | Lys | Val | Asn | Leu |
| Leu | Ser | Ala | Ile | Lys | Ser | Pro | Cys | His | Arg |
| Glu | Thr | Pro | Glu | Glu | Ala | Glu | Pro | Met | Ala |
| Trp | Tyr | Glu | Pro | Ile | Tyr | Leu | Gly | Gly | Val |
| Phe | Gln | Leu | Glu | Lys | Gly | Asp | Arg | Leu | Ser |
| Thr | Glu | Val | Asn | Gln | Pro | Glu | Tyr | Leu | Asp |
| Leu | Ala | Glu | Ser | Gly | Gln | Val | Tyr | Phe | Gly |
| Ile | Ile | Ala | Leu | | | | | | |

TABLE 3

```
          10           20           30    HaeII  40           50           60
          |            |            |       ↓   |            |            |
GGGGGGGGGGGGGGGGCCCTCTGGAGAGAGCGCCATGAGCACTGAGAGTATGATCCGGGAC
CCCCCCCCCCCCCCCGGGAGACCTCTCTCGCGGTACTCGTGACTCTCATACTAGGCCCTG 70           80           90          100          110          120
          |            |            |            |            |            |
GTCGAGCTGGCGGAGGGGCCGCTCCCCAAGAAGGCAGGGGGGCCCCAGGGCTCCAAGCGC
CAGCTCGACCGCCTCCCCGGCGAGGGGTTCTTCCGTCCCCCCGGGGTCCCGAGGTTCGCG
                                                                        HaeII ↑

130          140          150          160          170          180
          |            |            |            |            |            |
TGCCTCTGCCTCAGCCTCTTCTCTTTCCTGCTCGTGGCTGGAGCCACCACGCTCTTCTGC
ACGGAGACGAGTCGAGAAGAGAAAGGACGAGCACCGACCTCGTGTGCGAGAAGACG 190          200          210          220          230          240
          |            |            |            |            |            |
CTGCTGCACTTCAGGGTGATCGGCCCTCAGGAGGAAGAGCAGTCCCCAAACAACCTCCAT
GACGACGTGAAGTCCCACTAGCCGGGAGTCCTCCTTCTCGTCAGGGGTTTGTTGGAGGTA
```

TABLE 3-continued

```
         250         260         270         280    AvaI 290         300
          |           |           |           |      |    |           |
CTAGTCAACCCTGTGGCCCAGATGGTCACCCTCAGATCAGCTTC TCGGGCCCTGAGTGAC
GATCAGTTGGGACACCGGGTCTACCAGTGGGAGTCTAGTCGAAGAGCC CGGGACTCACTG 310         320         330         340         350         360
          |           |           |           |           |           |
AAGCCTCTAGCCCACGTAGTAGCAAACCCGCAAGTGGAGGGCCAGCTCCAGTGGCTGAGC
TTCGGAGATCGGGTGCATCATCGTTTGGGCGTTCACCTCCCGGTCGAGGTCACCGACTCG 370         380         390         400         410         420
          |           |           |           |           |           |
CAGCGTGCGAACGCCCTGCTGGCCAACGGCATGAAGCTCACGGACAACCAGCTGGTGGTG
GTCGCACGCTTGCGGGACGACCGGTTGCCGTACTTCGAGTGCCTGTTGGTCGACCACCAC 430         440         450         460         470         480
          |           |           |           |           |           |
CCGGCCGACGGGCTGTACCTCATCTACTCCCAGGTTCTCTTCAGCGGTCAAGGCTGCCGC
GGCCGGCTGCCCGACATGGAGTAGATGAGGGTCCAAGAGAAGTCGCCAGTTCCGACGGCG 490         500         510         520         530         540
          |           |           |           |           |           |
TCCTACGTGCTCCTCACTCACACTGTCAGCCGCTTCGCCGTCTCCTACCCGAACAAGGTC
AGGATGCACGAGGAGTGAGTGTGACAGTCGGCGAAGCGGCAGAGGATGGGCTTGTTCCAG 550         560         570         580         590         600
          |           |           |           |           |           |
AACCTCCTCTCTGCCATCAAGAGCCCCTGCCACCGGGAGACCC CCGA GGAGGCTGAGCCC
TTGGAGGAGAGACGGTAGTTCTCGGGGACGGTGGCCCTCTGGGGGCT CCTCCGACTCGGG
                                                 ↑
                                               AvaI 610         620         630         640         650         660
          |           |           |           |           |           |
ATGGCCTGGTACGAGCCCATCTACCTGGGCGGCGTCTTCCAGTTGGAGAAGGGTGACCGG
TACCGGACCATGCTCGGGTAGATGGACCCGCCGCAGAAGGTCAACCTCTTCCCACTGGCC 670         680         690         700         710         720
          |           |           |           |           |           |
CTCAGCACCGAGGTCAACCAGCCTGAGTACCTGGACCTTGCCGAGTCCGGGCAGGTCTAC
GAGTCGTGGCTCCAGTTGGTCGGACTCATGGACCTGGAACGGCTCAGGCCCGTCCAGATG 730         740         750         760         770         780
          |           |           |           |           |           |
TTTGGGATCCTTGCCCTGTGAGGGGACTGACCACCACTCCTCCCCCTCTCCCACCCCAGC
AAACCCTAGTAACGGGACACTCCCCTGACTGGTGGTGAGGAGGGGGAGAGGGTGGGGTCG 790         800
          |           |
CCCCTCACTCTGGGCGCCCTCAG
GGGGAGTGAGACCCGCGGGAGTC
```

TABLE 4

```
                    GACCCACGG
    -30        -20        -10         -1
     |          |          |          |
    CTCCACCCTCTCTCCCCTGGAAAGGACACC 1         10         20         30
      |          |          |          |
     ATGAGCACTGAAAGCATGATCCGGGACGTC
     Met Ser Thr Glu Ser Met Ile Arg Asp Val 40         60
                 |          |
     GAGCTGGCCGAGGAGGCGCTCCCCAAGAAG
     Glu Leu Ala Glu Glu Ala Leu Pro Lys Lys 80         90
                 |          |
     ACAGGGGGGCCCCAGGGCTCCAGGCGGTGC
     Thr Gly Gly Pro Gln Gly Ser Arg Arg Cys 100        110        120
                |          |          |
     TTGTTCCTCAGCCTCTTCTCCTTCCTGATC
     Leu Phe Leu Ser Leu Phe Ser Phe Leu Ile
```

TABLE 4-continued

```
               130        140        150
                |          |          |
     GTGGCAGGCGCCACCACGCTCTTCTGCCTG
     Val Ala Gly Ala Thr Thr Leu Phe Cys Leu 160        170        180
                |          |          |
     CTGCACTTTGGAGTGATCGGCCCCCAGAGG
     Leu His Phe Gly Val Ile Gly Pro Gln Arg 190        200        210
                |          |          |
     GAAGAGTTCCCCAGGGACCTCTCTCTAATC
     Glu Glu Phe Pro Arg Asp Leu Ser Leu Ile 220        230        240
                |          |          |
     AGCCCTCTGGCCCAGGCAGTCAGA TCATCT
     Ser Pro Leu Ala Gln Ala Val Arg Ser Ser 250        260        270
                |          |          |
     TCTCGAACCCCGAGTGACAAGCCTGTAGCC
     Ser Arg Thr Pro Ser Asp Lys Pro Val Ala
```

TABLE 4-continued

```
          280        290        300
           |          |          |
CATGTTGTAGCAAACCCTCAAGCTGAGGGG
His Val Val Ala Asn Pro Gln Ala Glu Gly 310        320        330
           |          |          |
CAGCTCCAGTGGCTGAACCGCCGGGCCAAT
Gln Leu Gln Trp Leu Asn Arg Arg Ala Asn 340        350        360
           |          |          |
GCCCTCCTGGCCAATGGCGTGGAGCTGAGA
Ala Leu Leu Ala Asn Gly Val Glu Leu Arg 370        380        390
           |          |          |
GATAACCAGCTGGTGGTGCCATCAGAGGGC
Asp Asn Gln Leu Val Val Pro Ser Glu Gly 400        410        420
           |          |          |
CTGTACCTCATCTACTCCCAGGTCCTCTTC
Leu Try Leu Ile Tyr Ser Gln Val Leu Phe 430        440        450
           |          |          |
AAGGGCCAAGGCTGCCCCTCCACCCATGTG
Lys Gly Gln Gly Cys Pro Ser Thr His Val 460        470        480
           |          |          |
CTCCTCACCCACACCATCAGCCGCATCGCC
Leu Leu Thr His Thr Ile Ser Arg Ile Ala 490        500        510
           |          |          |
GTCTCCTACCAGACCAAGGTCAACCTCCTC
Val Ser Tyr Gln Thr Lys Val Asn Leu Leu
```

TABLE 4-continued

```
          520        530        540
           |          |          |
TCTGCCATCAAGAGCCCCTGCCAGAGGGAG
Ser Ala Ile Lys Ser Pro Cys Gln Arg Glu 550        560        570
           |          |          |
ACCCCAGAGGGGGCTGAGGCCAAGCCCTGG
Thr Pro Glu Gly Ala Glu Ala Lys Pro Trp 580        590        600
           |          |          |
TATGAGCCCATCTATCTGGGAGGGGTCTTC
Tyr Glu Pro Ile Tyr Leu Gly Gly Val Phe 610        620        630
           |          |          |
CAGCTGGAGAAGGGTGACCGACTCAGCGCT
Gln Leu Glu Lys Gly Asp Arg Leu Ser Ala 640        650        660
           |          |          |
GAGATCAATCGGCCCGACTATCTCGACTTT
Glu Ile Asn Arg Pro Asp Tyr Leu Asp Phe 670        680        690
           |          |          |
GCCGAGTCTGGGCAGGTCTACTTTGGGATC
Ala Glu Ser Gly Gln Val Tyr Phe Gly Ile 700        710        720
           |          |          |
ATTGCCCTG TGAGGAGGACGAACATCCAAC
Ile Ala Leu 730        740
           |          |
CTTCCCAAACGCCTCCCCTGC
```

TABLE 5

```
                                                    30
ATGAGCACTGA A  AG C ATGATCCGGGACGT G
ATGAGCACTGA G  AG T ATGATCCGGGACGT C

60
GAGCTGGCCGAGG A G G CGCTCCCCAAGAAG
GAGCTGGCGGAGG G G C CGCTCCCCAAGAAG

90
A CAGGGGGGCCCCAGGGCTCCA G GCG G TGC
G CAGGGGGGCCCCAGGGCTCCA A GCG C TGC

120
T T G T T CCTCAGCCTCTTCTC C TTCCTG A TC
C T C T G CCTCAGCCTCTTCTC T TTCCTG C TC

150
GTGGC A GG C GCCACCACGCTCTTCTGCCTG
GTGGC T GG A GCCACCACGCTCTTCTGCCTG

180
CTGCACTT TG G A GTGATCGGCCC C CAG AG G
CTGCACTT CA G G GTGATCGGCCC T CAG GA G

210
GAAGAG --- T T CCC C A GGG ACCTC TC TCTA
GAAGAG CAG T C CCC A A ACA ACCTC CA TCTA

240
A TCA G CCCT C TGGCCCAG ------ G C AG TC
G TCA A CCCT G TGGCCCAG ATGGTCA C CC TC

270
AGATCA T CTTCTCG AA CCC C GAGTGACAAG
AGATCA G CTTCTCG GG CCC T GAGTGACAAG
```

TABLE 5-continued

```
    ┌─┐        ┌─┐┌─┐           ┌─┐      300
CCT │G│TAGCCCA│T││GT││T│GTAGCAAACCC│T│CAA
CCT │C│TAGCCCA│C││GT││A│GTAGCAAACCC│G│CAA
    └─┘        └─┘└─┘           └─┘

┌─┐  ┌────┐ ┌─┐              ┌─┐┌──┐      330
│G│CT│GAGGG│G│CAGCTCCAGTGGCTGA│A││CC│GC
│G│TG│GAGGG│C│CAGCTCCAGTGGCTGA│G││CC│AG
└─┘  └────┘ └─┘              └─┘└──┘
```

Upper rows: base sequence encoding human TNF precursor
Lower rows: base sequence encoding rabbit TNF precursor

```
┌──┐┌──┐┌──┐┌──┐┌─────┐┌────────┐┌─┐┌───┐┌─┐  360
│CG││G ││GC││C ││AA │T││GCCCT │C││CTGGCCAA│T││GGC││G│TG
│CG││T ││GC││G ││AA │C││GCCCT │G││CTGGCCAA│C││GGC││A│TG
└──┘└──┘└──┘└──┘└─────┘└────────┘└─┘└───┘└─┘

┌─┐┌────┐┌─┐┌──┐┌──┐┌─┐┌─────────────────┐    390
│G││AGCT││G││A ││GA││GA│T│AACCAGCTGGTGGTGCC│A
│A││AGCT││C││A ││CG││GA│C│AACCAGCTGGTGGTGCC│G
└─┘└────┘└─┘└──┘└──┘└─┘└─────────────────┘

┌─┐┌─┐┌──┐┌─┐┌──┐┌─┐┌───────────────────┐    420
│T││C││A ││GA││G ││GG││C│CTGTACCTCATCTACTCCCAG
│G││C││C ││GA││C ││GG││G│CTGTACCTCATCTACTCCCAG
└─┘└─┘└──┘└─┘└──┘└─┘└───────────────────┘

┌──┐┌─┐┌──────┐┌──┐┌──┐┌─┐┌──────────┐┌─┐┌────┐  450
│GT││C││CTCTTCA││AG││GG││C││CAAGGCTGCC │C│CTCC
│GT││T││CTCTTCA││GC││GG││T││CAAGGCTGCC │G│CTCC
└──┘└─┘└──────┘└──┘└──┘└─┘└──────────┘└─┘

┌────┐┌─┐┌─┐┌──────────┐┌─┐┌─────┐┌──┐┌────┐    480
│ACCC││A││T││GTGCTCCTCAC││C││CACAC││CA││TCAGC
│---T││A││C││GTGCTCCTCAC││T││CACAC││TG││TCAGC
└────┘└─┘└─┘└──────────┘└─┘└─────┘└──┘└────┘

┌───┐┌─┐┌──────────────┐┌─┐┌──┐┌─┐┌──────┐    510
│CGC││A││TCGCCGTCTCCTACC││A││GA││C││CAAGGTC
│CGC││T││TCGCCGTCTCCTACC││C││GA││A││CAAGGTC
└───┘└─┘└──────────────┘└─┘└──┘└─┘└──────┘

540
AACCTCCTCTCTGCCATCAAGAGCCCCTGC
AACCTCCTCTCTGCCATCAAGAGCCCCTGC

┌──┐┌──┐┌─────────┐┌─┐┌────────────┐┌─┐┌──┐   570
│CA││GA││GGGAGACCCC││A││GAGGGGGCTGAG││G││CC
│CA││CC││GGGAGACCCC││C││GAGGAGGCTGAG││C││CC
└──┘└──┘└─────────┘└─┘└────────────┘└─┘└──┘

┌─┐┌─┐┌─┐┌─────┐┌─┐┌──────────┐┌─┐┌────┐┌─┐  600
│A││A││G││C│CCTGGTA││T││GAGCCCATCTA││T││CTGGG││A
│A││T││G││G│CCTGGTA││C││GAGCCCATCTA││C││CTGGG││C
└─┘└─┘└─┘└─────┘└─┘└──────────┘└─┘└────┘└─┘

┌──┐┌─┐┌───────┐┌─┐┌────────────────┐┌─┐    630
│GG││G││GTCTTCCAG││C││TGGAGAAGGGTGACCG││A
│GG││C││GTCTTCCAG││T││TGGAGAAGGGTGACCG││G
└──┘└─┘└───────┘└─┘└────────────────┘└─┘

┌─────┐┌─┐┌─┐┌───┐┌─┐┌────┐┌─┐┌─┐┌───┐┌─┐┌──┐┌─┐  660
│CTCAGC││G││C││T│GAG│A││TCAA││T││C││G│GCC│C││GA││C││TA│T
│CTCAGC││A││C││C│GAG│G││TCAA││C││C││A│GCC│T││GA││G││TA│C
└─────┘└─┘└─┘└───┘└─┘└────┘└─┘└─┘└───┘└─┘└──┘└─┘

┌──┐┌─┐┌───┐┌─┐┌────────┐┌─┐┌─────────┐    690
│CT││C││GAC││T││TTGCCGAGTC││T││GGGCAGGTCTAC
│CT││G││GAC││C││TTGCCGAGTC││C││GGGCAGGTCTAC
└──┘└─┘└───┘└─┘└────────┘└─┘└─────────┘

***
TTTGGGATCATTGCCCTGTGA
TTTGGGATCATTGCCCTGTGA
```

Regions surrounded by a rectangle are a homologous region.
Mark "- - -" shows deletion of a codon.
Mark "***" shows a termination codon.

TABLE 6

| | | | | | | | | 10 |
|---|---|---|---|---|---|---|---|---|
| Met | Ser | Thr | Glu | Ser | Met | Ile | Arg | Asp Val |
| Met | Ser | Thr | Glu | Ser | Met | Ile | Arg | Asp Val |

| | | | | | | | 20 |
|---|---|---|---|---|---|---|---|
| Glu | Leu | Ala | Glu | Glu | Ala | Leu | Pro Lys Lys |
| Glu | Leu | Ala | Glu | Gly | Pro | Leu | Pro Lys Lys |

TABLE 6-continued

| | | | | | | 30 |
|---|---|---|---|---|---|---|
| Thr | Gly | Gly | Pro | Gln | Gly | Ser | Arg Arg Cys |
| Ala | Gly | Gly | Pro | Gln | Gly | Ser | Lys Arg Cys |

| | | | | | | | 40 |
|---|---|---|---|---|---|---|---|
| Leu | Phe | Leu | Ser | Leu | Phe | Ser | Phe Leu Ile |
| Leu | Cys | Leu | Ser | Leu | Phe | Ser | Phe Leu leu |

TABLE 6-continued

```
                                              50
Val Ala Gly Ala Thr Thr Leu Phe Cys Leu
Val Ala Gly Ala Thr Thr Leu Phe Cys Leu

60
Leu His Phe  Gly  Val Ile Gly Pro Gln  Arg
Leu His Phe  Arg  Val Ile Gly Pro Gln  Glu

70
Glu Glu  - - -  Phe  Pro  Arg Asp  Leu  Ser  Leu
Glu Glu  Gln    Ser  Pro  Asn Asn  Leu  His  Leu

80
Ile Ser  Pro  Leu  Ala Gln  - - - - - -  Ala Val
Val Asn  Pro  Val  Ala Gln  Met Val Thr   Leu

90
Arg Ser  Ser  Ser Arg  Thr Pro  Ser Asp Lys
Arg Ser  Ala  Ser Arg  Ala Leu  Ser Asp Lys

100
Pro  Val  Ala His Val Val Ala Asn Pro Gln
Pro  Leu  Ala His Val Val Ala Asn Pro Gln

110
Ala  Glu Gly Gln Leu Gln Trp Leu  Asn Arg
Val  Glu Gly Gln Leu Gln Trp Leu  Ser Gln

120
Arg Ala Asn Ala Leu Leu Ala Asn Gly  Val
Arg Ala Asn Ala Leu Leu Ala Asn Gly  Met
```

Upper rows: human TNF precursor
Lower rows: rabbit TNF precursor

```
                                             130
Glu  Leu  Arg  Asp Asn Gln Leu Val Val Pro
Lys  Leu  Thr  Asp Asn Gln Leu Val Val Pro

140
Ser Glu  Gly Leu Tyr Leu Ile Tyr Ser Gln
Ala Asp  Gly Leu Tyr Leu Ile Tyr Ser Gln

150
Val Leu Phe  Lys  Gly Gln Gly Cys  Pro  Ser
Val Leu Phe  Ser  Gly Gln Gly Cys  Arg  Ser

160
Thr His  Val Leu Leu Thr His Thr  Ile  Ser
- - - Tyr  Val Leu Leu Thr His Thr  Val  Ser

170
Arg  Ile  Ala Val Ser Tyr  Gln Thr  Lys Val
Arg  Phe  Ala Val Ser Tyr  Pro Asn  Lys Val

180
Asn Leu Leu Ser Ala Ile Lys Ser Pro Cys
Asn Leu Leu Ser Ala Ile Lys Ser Pro Cys

190
Gln  Arg Glu Thr Pro Glu  Gly  Ala Glu  Ala
His  Arg Glu Thr Pro Glu  Glu  Ala Glu  Pro

200
Lys Pro  Trp Tyr Glu Pro Ile Tyr Leu Gly
Met Ala  Trp Tyr Glu Pro Ile Tyr Leu Gly

210
Gly Val Phe Gln Leu Glu Lys Gly Asp Arg
Gly Val Phe Gln Leu Glu Lys Gly Asp Arg

220
Leu Ser  Ala  Glu  Ile  Asn Arg Pro  Asp Tyr
Leu Ser  Thr  Glu  Val  Asn Gln Pro  Glu Tyr

230
Leu Asp Phe  Ala Glu Ser Gly Gln Val Tyr
Leu Asp Leu  Ala Glu Ser Gly Gln Val Tyr
```

TABLE 6-continued

```
 Phe Gly Ile Ile Ala Leu
 Phe Gly Ile Ile Ala Leu
```

Regions surrounded by a rectangle are a homologous region.
mark "- - -" shows a deletion of an amino acid.

TABLE 7

| Amino acid | Relative molar quantities |
|---|---|
| Asp + Asn | 12.1 |
| Thr | 5.5 |
| Ser | 12.4 |
| Glu + Gln | 20.3 |
| Pro | 10.3 |
| Gly | 10.6 |
| Ala | 13.0 |
| Cys | 1.5 |
| Val | 12.1 |
| Met | <0.1 |
| Ile | 8.0 |
| Leu | 17.7 |
| Tyr | 6.8 |
| Phe | 3.9 |
| His | 2.8 |
| Lys | 6.1 |
| Arg | 7.5 |
| Trp | 1.6 |

TABLE 8

| Human Cell | Origin | | Ratio of growth inhibition |
|---|---|---|---|
| Normal cells: | | | |
| WI-38 | (ATCC CCL 75) | lung diploid | not inhibited |
| MRC-5 | (ATCC CCL 171) | lung diploid | not inhibited |
| IMR-90 | (ATCC CCL 186) | lung diploid | not inhibited |
| Tumor cells: | | | |
| G-361 | (ATCC CRL 1424) | melanoma | 75% |
| HT-1376 | (ATCC CRL 1472) | bladder carcinoma | 49% |
| ZR-75-1 | (ATCC CRL 1500) | breast carcinoma | 97% |
| HOS | (ATCC CRL 1543) | osteogenic sarcoma | 47% |
| WiDr | (ATCC CCL 218) | colon adenocarcinoma | 37% |
| MCF7 | (ATCC HTB 22) | breast adenocarcinoma | 69% |
| G-402 | (ATCC CRL 1440) | renal leiomyoblastoma | 98% |
| PANC-1 | (ATCC CRL 1469) | epitheloid carcinoma | 59% |
| HeLa | (ATCC CCL 2) | epitheloid carcinoma | 31% |

TABLE 9

```
              10          20          30
               |           |           |
        GGGGGGGGGGGGGGGGCCCTCTGGAGAGAGC 40          50          60
               |           |           |
        GCCATGAGCACTGAGAGTATGATCCGGGAC
           Met Ser Thr Glu Ser Met Ile Arg Asp 70          80          90
               |           |           |
        GTCGAGCTGGCGGAGGGGCCGCTCCCCAAG
        Val Glu Leu Ala Glu Gly Pro Leu Pro Lys
```

TABLE 9-continued

```
         100        110        120
          |          |          |
AAGGCAGGGGGGCCCCAGGGCTCCAAGCGC
Lys Ala Gly Gly Pro Gln Gly Ser Lys Arg 130        140        150
          |          |          |
TGCCTCTGCCTCAGCCTCTTCTCTTTCCTG
Cys Leu Cys Leu Ser Leu Phe Ser Phe Leu 160        170        180
          |          |          |
CTCGTGGCTGGAGCCACCACGCTCTTCTGC
Leu Val Ala Gly Ala Thr Thr Leu Phe Cys 190        200        210
          |          |          |
CTGCTGCACTTCAGGGTGATCGGCCCTCAG
Leu Leu His Phe Arg Val Ile Gly Pro Gln 220        230        240
          |          |          |
GAGGAAGAGCAGTCCCCAAACAACCTCCAT
Glu Glu Glu Gln Ser Pro Asn Asn Leu His 250        260        270
          |          |          |
CTAGTCAACCCTGTGGCCCAGATGGTCACC
Leu Val Asn Pro Val Ala Gln Met Val Thr 280        290        300
          |          |          |
CTCAGATCAGCTTCTCGGGCCCTGAGTGAC
Leu Arg Ser Ala Ser Arg Ala Leu Ser Asp 310        320        330
          |          |          |
AAGCCTCTAGCCCACGTAGTAGCAAACCCG
Lys Pro Leu Ala His Val Val Ala Asn Pro 340        350        360
          |          |          |
CAAGTGGAGGGCCAGCTCCAGTGGCTGAGC
Gln Val Glu Gly Gln Leu Gln Trp Leu Ser 370        380        390
          |          |          |
CAGCGTGCGAACGCCCTGCTGGCCAACGGC
Gln Arg Ala Asn Ala Leu Leu Ala Asn Gly 400        410        420
          |          |          |
ATGAAGCTCACGGACAACCAGCTGGTGGTG
Met Lys Leu Thr Asp Asn Gln Leu Val Val 430        440        450
          |          |          |
CCGGCCGACGGGCTGTACCTCATCTACTCC
Pro Ala Asp Gly Leu Tyr Leu Ile Tyr Ser 460        470        480
          |          |          |
CAGGTTCTCTTCAGCGGTCAAGGCTGCCGC
Gln Val Leu Phe Ser Gly Gln Gly Cys Arg 490        500        510
          |          |          |
TCCTACGTGCTCCTCACTCACACTGTCAGC
Ser Tyr Val Leu Leu Thr His Thr Val Ser 520        530        540
          |          |          |
CGCTTCGCCGTCTCCTACCCGAACAAGGTC
Arg Phe Ala Val Ser Tyr Pro Asn Lys Val 550        560        570
          |          |          |
AACCTCCTCTCTGCCATCAAGAGCCCCTGC
Asn Leu Leu Ser Ala Ile Lys Ser Pro Cys 580        590        600
          |          |          |
CACCGGGAGACCCCCGAGGAGGCTGAGCCC
His Arg Glu Thr Pro Glu Glu Ala Glu Pro 610        620        630
          |          |          |
ATGGCCTGGTACGAGCCCATCTACCTGGGC
Met Ala Trp Tyr Glu Pro Ile Tyr Leu Gly 640        650        660
          |          |          |
GGCGTCTTCCAGTTGGAGAAGGGTGACCGG
Gly Val Phe Gln Leu Glu Lys Gly Asp Arg 670        680        690
          |          |          |
CTCAGCACCGAGGTCAACCAGCCTGAGTAC
Leu Ser Thr Glu Val Asn Gln Pro Glu Tyr 700        710        720
          |          |          |
CTGGACCTTGCCGAGTCCGGGCAGGTCTAC
Leu Asp Leu Ala Glu Ser Gly Gln Val Tyr 730        740        750
          |          |          |
TTTGGGATCATTGCCCTGTGAGGGGACTGA
Phe Gly Ile Ile Ala Leu 760        770        780
          |          |          |
CCACCACTCCTCCCCCTCTCCCACCCCAGC 790        800
          |          |
CCCCTCACTCTGGGCGCCCTCAG
```

[VI] The following Examples and Referential Examples illustrate this invention more specifically. It should be understood however that the invention is in no way limited

BRIEF DESCRIPTION OF THE DRAWINGS

For a better understanding of the following examples.

FIG. 1 shows the restriction endonuclease cleavage sites used for preparing DNA fragments, and the directions and extents of sequencing for determination of the base sequence of the cloned cDNA encoding human TNF polypeptide [Example 1-(9)];

FIG. 2 shows a process of constructing an expression plasmid pHTT26 [Example 2-(1)];

FIG. 3 shows a process of constructing an expression plasmid pHTR91 [Example 2-(2)];

FIG. 4 shows a process of constructing an expression plasmid pHTS115 [Example 2-(3)];

FIG. 5 shows a process of constructing an expression plasmid pHTS37 [Example 2-(4)].

EXAMPLE 1

Figure 1:
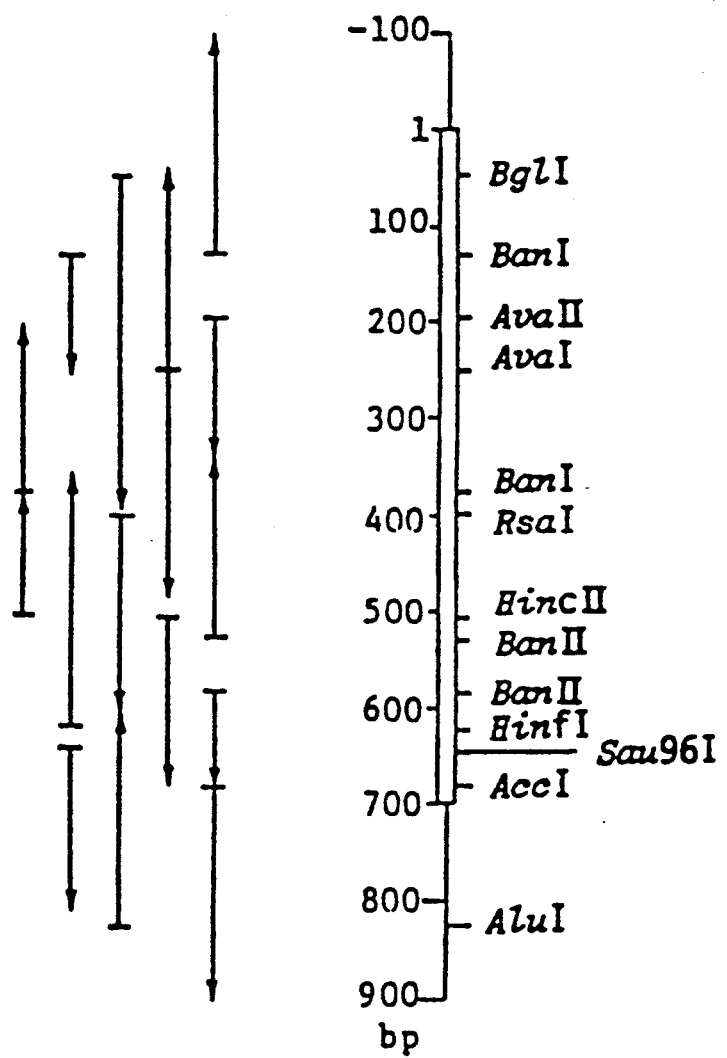
FIGS. 1 to 5 are attached to the present specification.

(1) Preparation of TNF mRNA from Human Alveolar Macrophages

Human alveolar macrophages were collected by broncho-alveolar lavage with phosphate buffered saline. The alveolar macrophages, $6.3 \times 10^7$ cells, were suspended in RPMI-1640 medium containing 10% fetal bovine serum, and seeded in Petri dishes (8 cm in diameter) at a cell density of $9 \times 10^6$ cells per dish. They were precultivated at 37° C. in a fully humidified atmosphere containing 5% carbon dioxide. After 1 hour cultivations endotoxin (lipopolysaccharide derived from *E. coli*), TPA (phorbol-12-myristate-13-acetate) and cycloheximide (protein synthesis inhibitor) were added to the dishes so that their final concentrations became 10 micrograms/ml, 10 ng/ml and 1 microgram/ml, respectively. The cultivation was further continued for 4 to 4.5 hours (total of 5 to 5.5 hours). The culture medium was removed by suction, and the macrophages adhered to the dishes were lysed and homogenized in a 5M guanidyl thiocyanate solution containing 0.6% sodium N-lauroyl sarcosinate and 6 mM sodium citrate. The homogenate was loaded on a 5.7M cesium chloride solution containing 0.1M EDTA, and centifuged for 20 hours at 26,500 rpm using an ultracentrifuge (RPS27-2 rotor, Hitachi Koki) to obtain a total RNA fraction as pellets. The pellets were dissolved in a small amount of 7M urea solution containing 0.35M NaCl, 20 mM Trim-HCl (pH 7.4) and 20 mM EDTA, and recovered by precipitation from ethanol. One hundred and fifty-nine micrograms of total RNA was obtained.

The total RNA fraction was dissolved in 1 ml of 10 mM Tris-HCl (pH 7.4) buffer containing 1 mM EDTA (to be referred to as TE solution), and the solution was heated at 65° C. for 5 minutes. A NaCl solution was added to a final concentration of 0.5M, and the solution was applied onto a column of oligo(dT)-cellulose previously equilibrated with the TE solution containing 0.5M NaCl. Poly(A)mRNA was eluted from the column with the TE solution in an yield of micrograms.

The poly(A)mRNA was dissolved to a concentration of 1.9 ng/nl in distilled water, and the solution was s injected into the oocytes of *Xenopus laevis* at a dose of about 50 nl per oocyte by a microinjection method. Ten oocytes were incubated in 100 microliters of the Barth's medium [*J. B. Gurdon, J. Embryol, Exp. Morphol.*, 20, 401 (1968)) at 22° C. for 24 hours. The oocytes were homogenized, and centrifuged at 10,000 rpm for 10 minutes. The supernatant was subjected to assay of TNF activity by determining the cytotoxic activity against mouse L-929 cells.

The method of measuring the cytotoxic activity against L-929 cells was as follows:

A sample (0.1 ml) diluted serially with the below-mentioned a medium and 0.1 ml of a suspension of L-929 cells ($5 \times 10^5$ cells/ml) containing actinomycin D (2 micrograms/ml) were added into each well of a 96 well multi-well plate (Flow Labs.). The Eagle's minimum essential medium containing 1% fetal bovine serum was used. The plate was incubated at 38.5° C. for 18 hours in a fully humidified atmosphere containing 5% carbon dioxide.

Procedures for determining the number of viable L-929 cells and estimating the biological activity were the same as those of the cytotoxic activity assay using mouse L-M cells as a target cell as mentioned in section [III-2-(1)].

The cytotoxic activity against L-929 cells determined under the above conditions was represented by "units (L-929)" to distinguish from the cytotoxic activity against mouse L-M cells.

The supernatant prepared as above had a cytotoxic activity of 6.6 units (L-929)/ml. It indicates that the poly(A)mRNA preparation contains TNF mRNA.

(2) Synthesis of cDNA

Complementary DNA was synthesized according to the method of Gubler and Hoffman [(Gener 25, 263 (1983)] using the poly(A)mRNA obtained in section (1) as a template.

Six micrograms of the poly(A)mRNA was dissolved in 40 microliters of 50 mM Tris-HCl (pH 8.3) buffer containing 10 mM MgCl$_2$, 10 mM dithiothreitol, 4 mM sodium pyrophosphate, 1.25 mM of each of the three deoxyribonucleotide triphosphates, dGTP, dATP and dTTP, 0.5mM dCTP, 167 nM alpha-$^{32}$P-dCTP (specific radioactivity, 3,000 Ci/mmole), 4 micrograms of oligo(dt)$_{12-18}$ and 120 units of reverse transcripase derived from avian myeloblastosis virus (AMV), and incubated at 43° C. for 30 minutes. Then, the reaction was stopped by adding EDTA. The reaction mixture was extracted with phenol/chloroform (1:1), and ammonium acetate was added to the aqueous phase to a final concentration of 2.5M. The resulting cDNA-mRNA hybrid was recovered from the aqueous phase by precipitation from ethanol. The cDNA-mRNA hybrid precipitate was dissolved in 100 microliters of 20 mM Tris-HCl (pH 7.5) buffer containing 5 mM MgCl$_2$, 10 mM (NH$_4$)$_2$SO$_4$, 100 mM KCl, 0.15 mM betanicotinamide-adenine dinucleotide, 5 micrograms of bovine serum albumin, 0.04 mM of each of four deoxyribonucleotide triphosphates, dGTP, dATP, dTTP and dCTP, 0.9 unit of *E. coli* ribonuclease H and 23 units of *E. coli* DNA polymerase I, and incubated at 12° C. for 60 minutes and further at 22° C. for 60 minutes to synthesize a dscDNA. The reaction was stopped by adding EDTA. The dscDNA was extracted with phenol/chloroform, and recovered by precipitation from ethanol as shown above.

(3) Preparation of oligo(dC)-tailed cDNA

The dscDNA obtained as above was dissolved in 100 microliters of 100 mM sodium cacodylate (pH 7.2) buffer containing 2 mM CoCl$_2$, 0.2 mM dithiothreitol, 0.1 mM alpha-$^{32}$P-dCTP (specific radioactivity, 3 Ci/mmole) and 10 units of terminal deoxynucleotidyl transferase, and incubated at 37° C. for 30 minutes to permit the addition of oligo(dc) tails to the 3'-termini of dscDNA.

The reaction was stopped by adding EDTA. The oligo(dC)-tailed dscDNA was extracted with phenol/chloroform, and recovered by precipitation from ethanol. The oligo(dC)-tailed dscDNA was dissolved in 10 mm Tris-HCl (pH 7.4) buffer containing 1 mM EDTA and 100 mM NaCl so that it contained 2 micrograms of the oligo(dC)-tailed dscDNA per ml.

(4) Preparation of oligo(dG)-tailed pBR322 DNA

Ten micrograms of pBR322 DNA was dissolved in 100 microliters of 20 mM Tris-HCl (pH 7.4) buffer containing 10 mM MgCl$_2$, 50 mM (NH$_4$)$_2$SO$_4$ and 10 micrograms of bovine serum albumin, and 15 units of the restriction endonuclease PstI was added. The mixture was incubated at 37° C. for 1 hour. After the reaction was terminated, the reaction mixture was extracted with phenol/chloroform, and the resulting DNA was recovered from the aqueous phase by precipitation from ethanol. The DNA obtained was dissolved in 200 microliters of the same reaction buffer as used for tailing of the dscDNA above (except that it contained 80 units of terminal deoxynucleotidyl transferase and $^3$H-dGTP instead of $^{32}$P-dCTP ed at 37° C. for 20 minutes to add about 10–15 deoxyguanylic acid (dG) residues to the 3'-termini. The reaction mixture was extracted with phenol/chloroform, and the oligo(dG)-tailed pBR322 DNA was recovered from the aqueous phase by ethanol precipitation. The resulting tailed PBR322 DNA was dissolved in the same buffer as used for dissolving the oligo(dC)-tailed dscDNA so that it contained the tailed pBR322 DNA at a concentration of 20 micrograms per ml.

(5) Construction of recombinant plasmids

One hundred and twenty microliters of the oligo(dC)-tailed cDNA solution was mixed with an equal volume of the oligo(dG)-tailed pBR322 DNA solution, and the mixture was incubated sequentially at 65° C. for 5 minutes and at 57° C. for 120 minutes to perform annealing and to construct recombinant plasmids.

(6) Selection of transformants

E. coli χ1776 strain was transformed with the recombinant plasmids obtained as above.

Specifically, E. coli χ1776 was cultivated at 37° C. in 20 ml of L broth (composition: 10 g of trypton, 5 g of yeast extract, 5 g of NaCl and 1 g of glucose per liter; pH 7.2) supplemented with 100 micrograms/ml of diaminopimelic acid and 40 micrograms/ml of thymidine until the turbidity at 600 nm reached 0.5. The cells were collected by centrifugation at 4° C., and washed with 10 ml of 10 mM Tris-HCl (pH 7.3) buffer containing 50 mM $CaCl_2$. The cells were resuspended in 2 ml of the same buffer as used above, and left to stand at 0° C. for 5 minutes. To 0.2 ml of the suspension was added 0.1 ml of the recombinant plasmids solution obtained as above. The mixture was left to stand at 0° C. for 15 minutes and then maintained at 42° C. for 2 minutes. Then, 0.5 ml of the supplemented L broth as used above was added, and cultivation was carried out with shaking for 1 hour. An aliquot of the culture was taken, spread on the supplemented L broth agar plate containing 15 micrograms/ml of tetracycline, and cultivated at 37° C. for about 12 hours. A cDNA library was prepared by selecting transformants resistant to tetracycline.

(7) Cloning of human TNF cDNA

Transformants harboring the recombinant plasmids containing cDNAs encoding human TNF polypeptide were selected from the cDNA library obtained in section (6), by a colony hybridization assay using DNA fragments prepared from the cloned cDNA encoding rabbit TNF as probes.

Specifically, the cDNA encoding rabbit TNF was isolated from the recombinant plasmid pRTNF802 as shown in Referential Example 1. Its base sequence is shown in Table 3. The cDNA was digested with the restriction endonuclease AvaI or HaeII. The digested DNA fragments were recovered by precipitation from ethanol. They were subjected to polyacrylamide gel electrophoresis to isolate desired DNA fragments.

The DNA fragment (299 bp) corresponding to the 285th to the 583rd bases as shown in Table 3 was obtained by digestion with the restriction endonuclease AvaI (to be referred to as AvaI fragment). Another DNA fragment (88 bp) corresponding to the 33rd to the 120th bases as shown in Table 3 was obtained by digestion with the restriction endonuclease HaeII (to be referred to as HaeII fragment). The AvaI fragment and HaeII fragment were labelled with $^{32}P$. These labelled DNA fragments were used as a probe for screening the cDNA library to select transformants having a plasmid containing cDNA encoding human TNF polypeptide by the colony hybridization assay according to the method of Hanahan and Meselson, 10, 63 (1980)].

Out of about 20,000 clones, 43 clones were selected by the 1st screening using the $^{32}P$-labelled AvaI fragment as a probe. Furthermore, these 43 selected clones were subjected to 2nd screening using the $^{32}P$-labelled HaeII fragment as a probe.

Finally, 6 clones harboring the recombinant plasmids having cDNAs which strongly hybridized with both it the rabbit TNF cDNA fragments were selected by these assays.

(8) Expression

Recombinant plasmid DNAs were isolated by the method of Wilkie et al. [Nucleic Acid Res., 7, 859 (1979)] from the six transformants selected in section (7); named plasmid No. pHTNF1, pHTNF4, pHTNF5, pHTNF13, pHTNF22 and pHTNF26, respectively. Each of the recombinant plasmids was introduced into E. coli HB101 according to the same method as shown in section (6) to prepare transformants harboring the recombinant plasmids.

The transformants were cultivated in 50 ml of LB broth [composition: 10 g of trypton, 5 g of yeast extract and 10 g of NaCl per liter; pH 7.51 until the turbidity at 600 nm of the culture reached about 0.8. Then, about 3 to $5 \times 10^{10}$ cells were collected. The cells were lysed by the method of Nagata et al. [Nature, 284, 316 (1980)] with slight modifications. The cells were resuspended in 1 ml of 50 mM Tris-HCl (pH 8.0) buffer containing 0.1% lysozyme and 30 mM NaCl. After standing for 30 minutes in ice water, the cells were lysed by repeating freezing-thawing 6 times. The cell debris was removed by centrifugation to give a clarified lysate. The lysate obtained from each transformant was subjected to assay of cytotoxic activity against L-929 cells.

It was consequently found that the lysate obtained from the transformant harboring plasmid pHTNF13 had a cytotoxic activity of 186.1 units (L-929)/ml.

(9) Determination of the base sequence of the cloned cDNA

The recombinant plasmid pHTNF13 was isolated as above. The plasmid DNA was cleaved with the restriction endonuclease PstI to isolate a cloned cDNA inserted into a vector. The cloned cDNA fragment was further cleaved with various restriction endonucleases, and the base sequences of the resulting 16 fragments were determined by the Maxam-Gilert method.

FIG. 1 shows the restriction endonuclease cleavage sites used for preparing the fragments, and the directions of sequencing indicated by arrows. The rectangular area is a coding region of human TNF precursor polypeptide. Table 4 shows the base sequence determined and the amino acid sequence deduced from the base sequence. The region encoding human TNF polypeptide was determined on the basis of homology to the base sequence encoding rabbit TNF.

The DNA encoding human TNF polypeptide codes for its precursor polypeptide consisting of 233 amino acid residues. The mature human TNF polypeptide is a polypeptide corresponding to the 155 amino acid residues from the carboxy-terminus of its precursor, which is coded in the base sequence from base No. 235 to base No. 699 in Table 4 (the region bracketed in Table 4). A termination codon followed by the last codon encoding human TNF polypeptide is an opal codon TGA.

(10) Immunological property of human TNF polypeptide

The immunological cross-reactivity of human TNF polypeptide in the lysate obtained above with anti-rabbit plasma TNF antibody was tested as follows:

The lysate was mixed with an equal volume of a 100-fold dilution of the purified anti-rabbit plasma TNF antibody obtained in Referential Example 4. After incubating at 37° C. for 2 hours, the cytotoxic activity of the reaction mixture was measured by the method described above using L-929 cells as a target cell. Rabbit plasma TNF obtained in Referential Example 2 was previously diluted with phosphate buffered saline and the dilution was used as a control TNF preparation. As the result below shows, the cytotoxic activity of human TNF polypeptide was not neutralized with the antibody.

| Sample | Anti-rabbit plasma TNF antibody | Cytotoxic activity* units (L-929)/ml |
|---|---|---|
| Lysate from the transformant harboring plasmid pHTNF13 | not added added | 186.1 191.0 |
| Rabbit plasma TNF | not added added | 572.3 <0.1 |

*Cytotoxic activity was shown as the activity in the original sample solution used for the test.

EXAMPLE 2

Production of human TNF polypeptide in *Escherichia coli*

(1) Expression under the control of tac promoter

The cloned cDNA was isolated from the recombinant plasmid pHTNF13 as mentioned in Example 1. The cDNA was further digested with the restriction endonuclease EcoRI to split off a part of the non-coding region downstream of the TNF coding region. The resulting DNA fragment (about 1.1 kbp) was inserted into a larger DNA fragment prepared from plasmid pBR322 by digestion with the restriction endonucleases PstI and EcoRI to construct a recombinant plasmid including TNF cDNA and a tetracycline-resistance gene, which was named pHT113.

Figure 2:
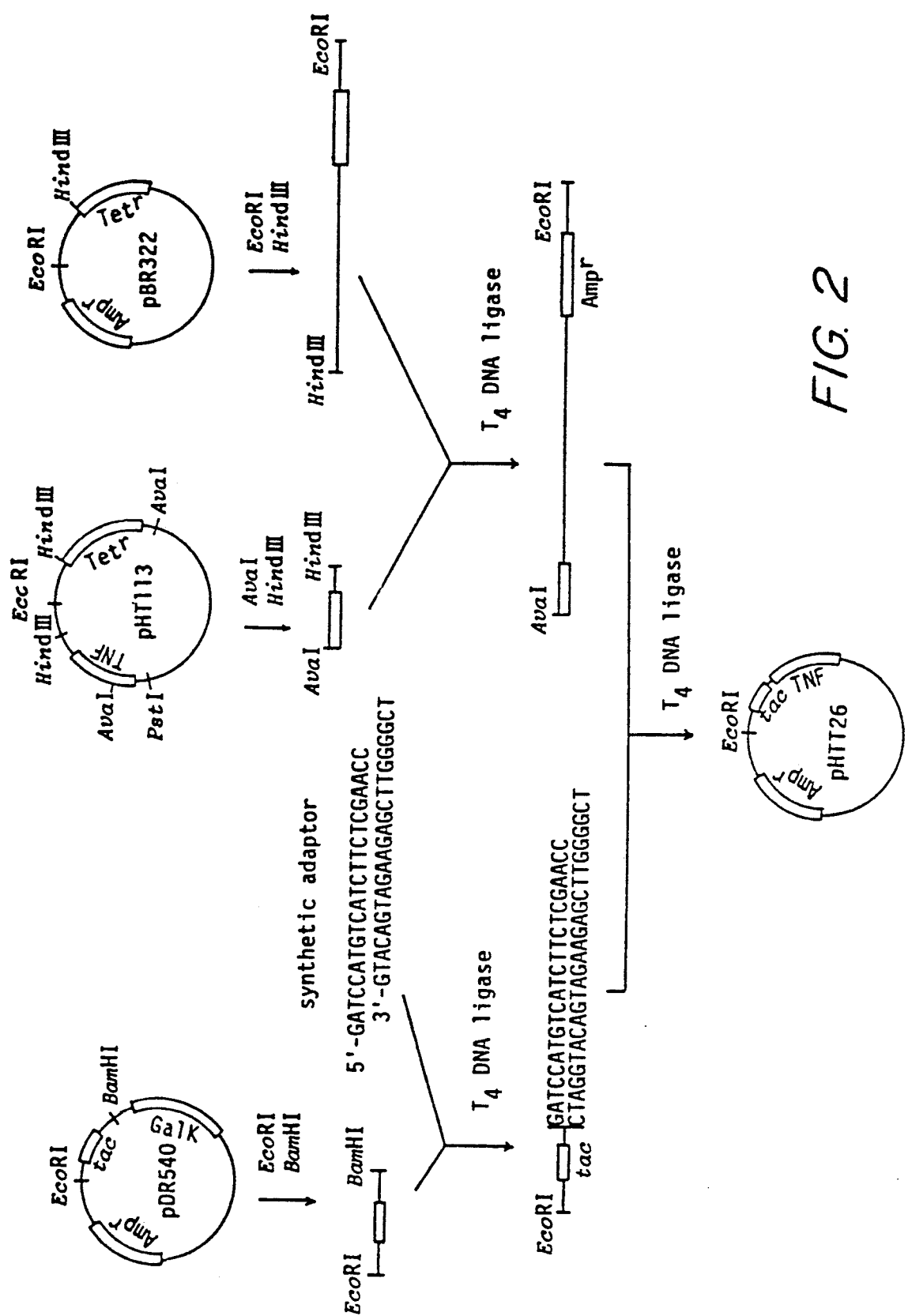

An expression plasmid pHTT26 carrying a cDNA encoding the mature human TNF polypeptide was constructed by the procedure illustrated in FIG. 2.

The cDNA isolated from pHT113 was digested with the restriction endonucleases AvaI and HindIII and the resulting DNA fragment (578 bp) including most of the coding region for the mature human TNF polypeptide (to be referred to as HTNF fragment) was isolated by polyacrylamide gel electrophoresis.

A DNA fragment including a tac promoter region was isolated as follows: Plasmid DNA (300 micrograms) of pDR540 [P-L Biochemicals; Russell, D. R., et al., Gene, 20, 231 (1982)] was dissolved in 2 ml of 10 mM Tris-HCl (pH 7.5) buffer containing 50 mM NaCl, 6 mM MgCl$_2$ and 6 mM 2-mercaptoethanol and digested with the restriction endonucleases EcoRI and BamHI by incubating at 37° C. for 60 minutes. After adding NaCl to give a final concentration of 0.3M, the digested DNA fragments were recovered from ethanol. The DNA fragment including a tac promoter region was isolated by polyacrylamide gel electrophoresis in an yield of 8.3 micrograms.

The tac promoter fragment was ligated with a chemically synthesized oligodeoxyribonucleotide adaptor represented by the following formula:

This adaptor includes an initiation codon ATG and a base sequence corresponding to the 5'-terminal portion of the base sequence encoding the mature human TNF polypeptide, and has the BamHI and AvaI cohesive termini. The resulting DNA fragment is referred to as tac promoter-adaptor fragment.

Separately, a larger DNA fragment (about 4.3 kbp) including an ampicillin-resistance gene (to be referred to as pBR322-Amp$^r$ fragment) was cut out from plasmid pBR322 by digestion with the restriction endonucleases HindIII and EcoRI, and isolated by gel electrophoresis using a low melting agarose (0.7%).

One microgram of the HTNF fragment and 6 micrograms of the pBR322-Amp$^r$ fragment were dissolved in 66 mM Trim-HCl (pH 7.6) buffer containing 6.6 mM MgCl$_2$ and incubated at 55° C. for 10 minutes. Then ATP and dithiothreitol were added to 1 mM and 10 mM respectively, and 168 units of T$_4$ DNA ligase was added and further the mixture was incubated at 22° C. for 120 minutes. The resulting DNA fragment was recovered by extraction with phenol in an yield of about 4 micrograms. The DNA fragment (0.8 microgram) was ligated with the tac promoter-adaptor fragment (0.3 microgram) under the same conditions as above except for using 63 units of T$_4$ DNA ligase. The reaction mixture was diluted to 6 fold with distilled water and mixed with an equal volume of the suspension of *E. coli* JM103 cells (P-L Biochemicals) treated with calcium as shown below. The mixture was sequentially incubated in ice water for 20 minutes, at 42° C. for 1 minute and at room temperature for 10 minutes, and LB broth was added. The mixture was shaken at 37° C. for 60 minutes. An aliquot of the resulting cell suspension was spread on LB agar plates containing 25 micrograms/ml of ampicillin, and cultivated overnight at 37° C. The ampicillin-resistance colonies were selected.

One of the transformants capable of producing human TNF polypeptide was named JM103/pHTT26.

The calcium-treated *E. coli* JM103 cells were prepared as follows: *E. coli* JM103 cells were inoculated in 5 ml of L broth and cultivated overnight at 37° C. One ml of the resulting culture was inoculated in 100 ml of LB broth and further cultivated at 37° C. until the turbidity at 650 nm of the culture reached 0.6. After standing for 30 minutes in ice water, the cells were collected by centrifugation and suspended in 50 ml of 50 mM CaCl$_2$, followed by standing at 0° C. for 60 minutes. The cells were collected by centrifugation and again suspended in 10 ml of 50 mM CaCl$_2$ containing 20% glycerol, which was used as the calcium-treated *E. coli* JM103 cells.

The transformant JM103/pHTT26 was cultivated overnight in LB broth at 37° C. The culture (0.5 ml) was inoculated in 5 ml of fresh LB broth and further cultivated at 37° C. for 1 hour. Then, isopropyl beta-D-thiogalactoside was added to a final concentration of 1 mM, and the cultivation was continued further for 4 hours. The cells were collected and suspended in 1 ml of 50 mM Tris-HCl (pH 8.0) buffer containing 0.1% lysozyme and 30 mM NaCl and left to stand at 0° C. for 30 minutes. Then freezing on a dry ice/ethanol bath and thawing at 37° C. were repeated 6 times, and the cell debris was removed by centrifugation to give a clarified lysate.

The lysate had a cytotoxic activity of 9.9 × 10$^4$ units (L-929)/ml. This cytotoxic activity was not neutralized with an antibody to rabbit plasma TNF as shown in Referential Example 4. It was confirmed that human TNF polypeptide did not cross-react with rabbit plasma TNF immunologically.

(2) Expression under the control of trp promoter

Figure 3:
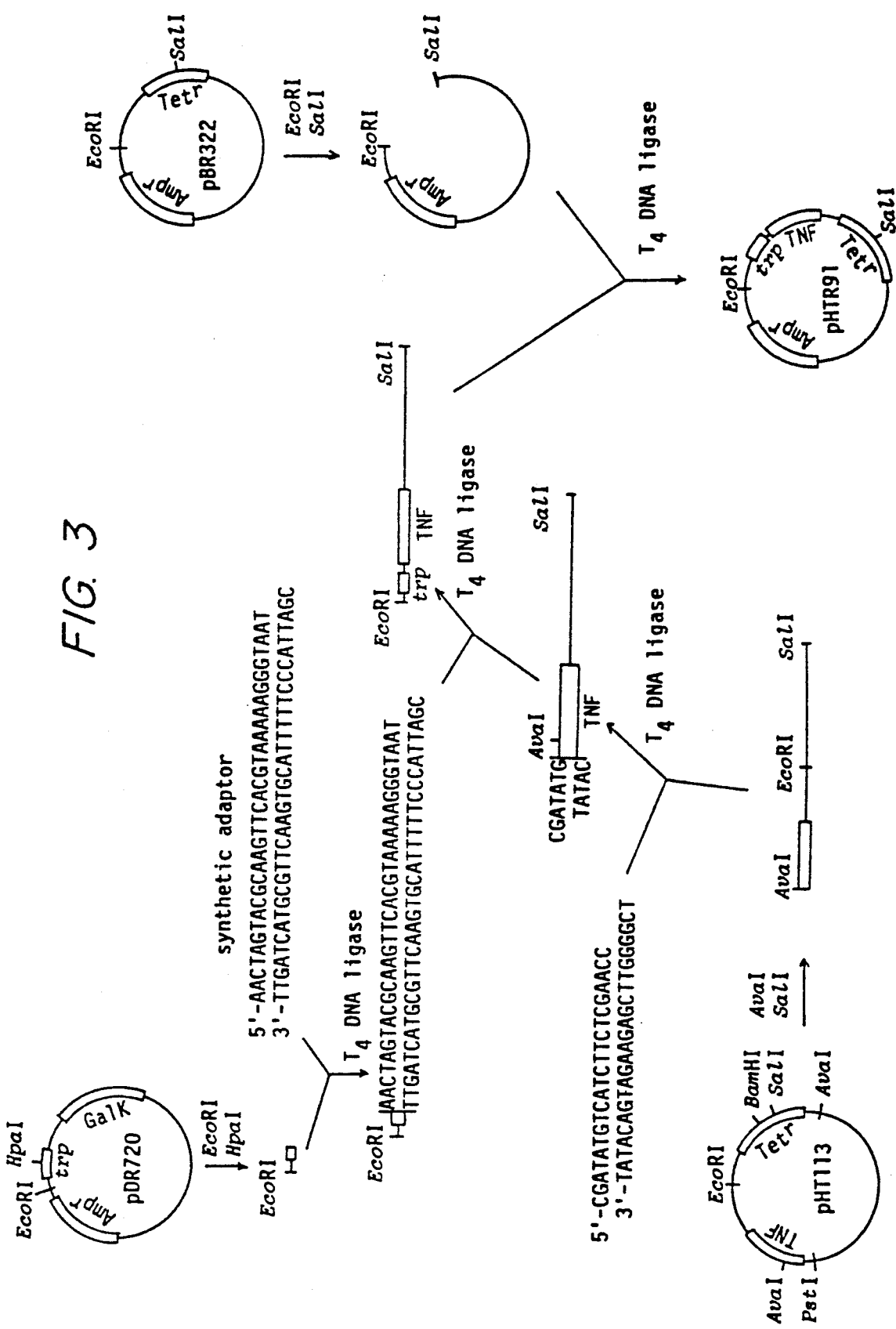

An expression plasmid pHTR91 was constructed by the procedure illustrated in FIG. 3.

The recombinant plasmid pHT113 was digested with the restriction endonucleases AvaI and SalI to be cut into 3 fragments (about 0.8 kbp, 1.3 kbp and 2.6 kbp in size). The 1.3 kbp-DNA fragment including most of the coding region for the mature human TNF polypeptide and a part of tetracycline-resistance gene was isolated (to be referred to as AvaI-SalI fragment). The AvaI-SalI fragment was ligated with the following chemically synthesized oligodeoxyribonucleotide adaptor. This adaptor was referred to as adaptor I.

5-CGATATGTCATCTTCTCGAACC
3'-TATACAGTAGAAGAGCTTGGGGCT

The resulting DNA fragment was referred to as HTNF-adaptor fragment.

Separately, the DNA fragment (35 bp) including a part of trp promoter region was cut out from a plasmid pDR720 [P-L Biochemicals; Russell, D. R., et al., Gene, 20, 231 (1982)] by digesting with the restriction endonucleases EcoRI and HpaI, and the DNA fragment was ligated with a chemically synthesized adaptor represented by the following formula:

5'-AACTAGTACGCAAGTTCACGTAAAAAGGGTAAT
3'-TTGATCATGCGTTCAAGTGCATTTTTCCCATTAGC

The ligated DNA fragment was referred to as promoter fragment.

Plasmid PBR322 was digested with the restriction endonucleases EcoRI and SalI, and a larger DNA fragment (about 3.7 kbp) was isolated. By sequential ligation of these three DNA fragments, the HTNF-adaptor fragment, the trp promoter fragment and the larger pBR322 fragment, an expression plasmid pHTR91 was constructed. The expression plasmid was introduced into E. coli HB101 cells by the method described in section (1), and one of the transformants was named HB101/pHTR91.

The transformant HB101/pHTR91 was cultivated overnight at 37° C. in the modified M-9 medium (composition: 0.7% Na2HPO4 12H2O, 0.3% KH2PO4, 0.05% NaCl, 0.1% NH4Cl, 2 mg/l of vitamin. B1, 0.45% casamino acid, 1 mM MgSO4, 0.1 mM CaCl2 and 0.5% glucose). The culture (0.05 ml) was inoculated in 5 ml of the same medium, and cultivated at 37° C. for 1 hour. Then, 3-beta-indoleacrylic acid was added to give a final concentration of 20 micrograms/ml, and cultivation was continued for 4 hours. The cells were collected and treated by the same procedure as described in section (1) to obtain a clarified lysate.

The lysate had a cytotoxic activity of 1.01 × 10^6 units (L-929)/ml.

(3) Expression under the control of phoS promoter

Figure 4:
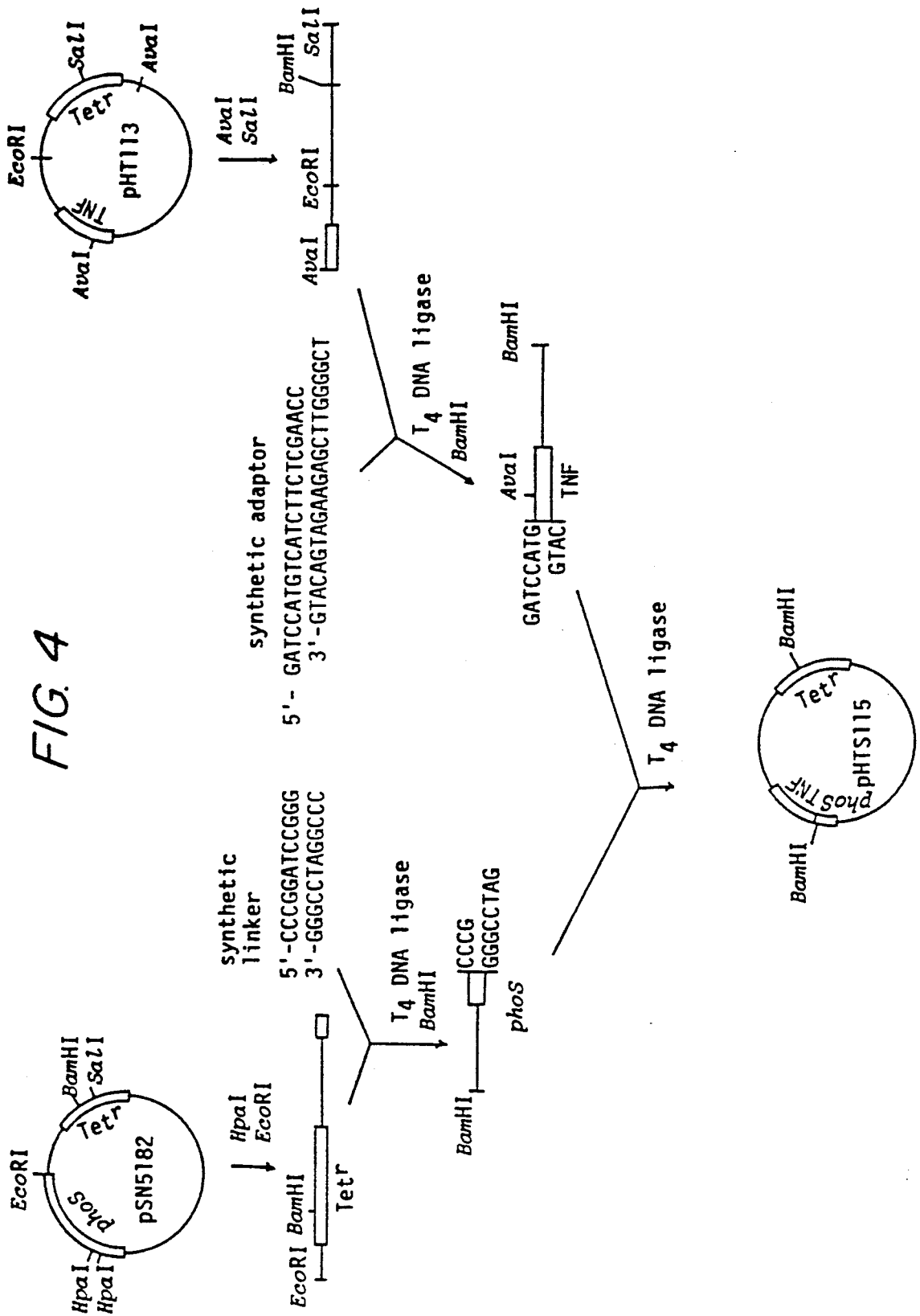

An expression plasmid pHTS115 capable of producing human TNF polypeptide fused with the signal peptide and the N-terminal portion of a phosphate binding protein, and secreting the fused protein into the periplasms of host cells was constructed by the procedure illustrated in FIG. 4.

The AvaI-SalI fragment obtained in section (2) was ligated with a chemically synthesized oligodeoxyribonucleotide adaptor having the following sequence:

5'-GATCCATGTCATCTTCTCGAACC
3'-GTACAGTAGAAGAGCTTGGGGCT

The ligated DNA fragment was digested with the restriction endonuclease BamHI to prepare a DNA fragment having BamHI cohesive termini at both ends (to be referred to as HTNF-Tet^r.BamHI fragment).

Separately, plasmid pSN5182 [Morita, T., et al., Eur. J. Biochem., 130, 427 (1983)] containing a phoS gene was digested with the restriction endonucleases HpaI and EcoRI to prepare the DNA fragment (about 4 kbp) including the phoS promoter region and Shine-Dalgarno sequence, the DNA sequence coding for the signal peptide and the N-terminal portion of a phosphate binding protein, and the tetracycline-resistance gene. This DNA fragment was referred to as HpaI-EcoRI fragment. The HpaI-EcoRI fragment was ligated with a chemically synthesized oligodeoxyribonucleotide linker having the following sequence:

5'-CCCGGATCCGGG
3'-GGGCCTAGGCCC

Then, the ligated DNA fragment was digested with the restriction endonuclease BamHI. The resulting DNA fragment (about 3.6 kbp) having BamHI cohesive termini at the both ends was referred to as phoS promoter-BamHI.Tet^r fragment.

The HTNF-Tet^r.BamHI fragment was ligated with the phoS promoter-BamHI.Tet^r fragment to construct an expression plasmid for producing the human TNF polypeptide fused with a phosphate binding protein, which was named pHTS115. The expression plasmid was introduced into E. coli HB101 according to the method as shown above.

One of the transformants (HB101/pHTS115) was cultivated in 5 ml of TG medium [composition: 120 mM TrisHCl (pH 7.4) buffer containing 0.2% glucose, 80 mM NaCl, 20 mM KCl, 20 mM NH4Cl, 3 mM Na2SO4, 0.2 mM CaCl2, 200 mM FeCl3, 20 mg/l of leucine, 20 mg/l of proline and 10 mg/l of vitamin, B1], supplemented with 0.64 mM KH2PO4, at 37° C. for 20 hours with shaking. The cells were collected by centrifugation, resuspended in 2 ml of TG medium supplemented with 0.064 mM KH2PO4 and cultivated at 37° C. for 6 hours. The cells were collected by centrifugation, and washed with 1 ml of 10 mM Tris-HCl (pH 7.2) buffer containing 30 mM NaCl. Then they were resuspended in 0.2 ml of 33 mM Trim-HCl (pH 7.2) buffer and mixed with an equal volume of 33 mM Tris-HCl (pH 7.2) buffer containing 0.1 mM EDTA and 40% sucrose. After incubation at 37° C. for 10 minutes, the cells were collected and resuspended in 0.1 ml of chilled 0.5 mM MgCl2 and left to stand in ice water for 10 minutes with occasional shaking. The cell debris was removed by centrifugation to obtain a clarified extract (to be referred to as periplasmic extract).

The periplasmic extract has a cytotoxic activity of 1.34 × 10^5 units (L-929)/ml.

The molecular weight of the polypeptide having cytotoxic activity was determined to be 19,000 daltons by sodium dodecylsulfate (SDS)-polyacrylamide gel (12.5%) electrophoresis, which suggests that the polypeptide produced was a fused protein.

(4) Expression under the control of phoS promoter

Figure 5:
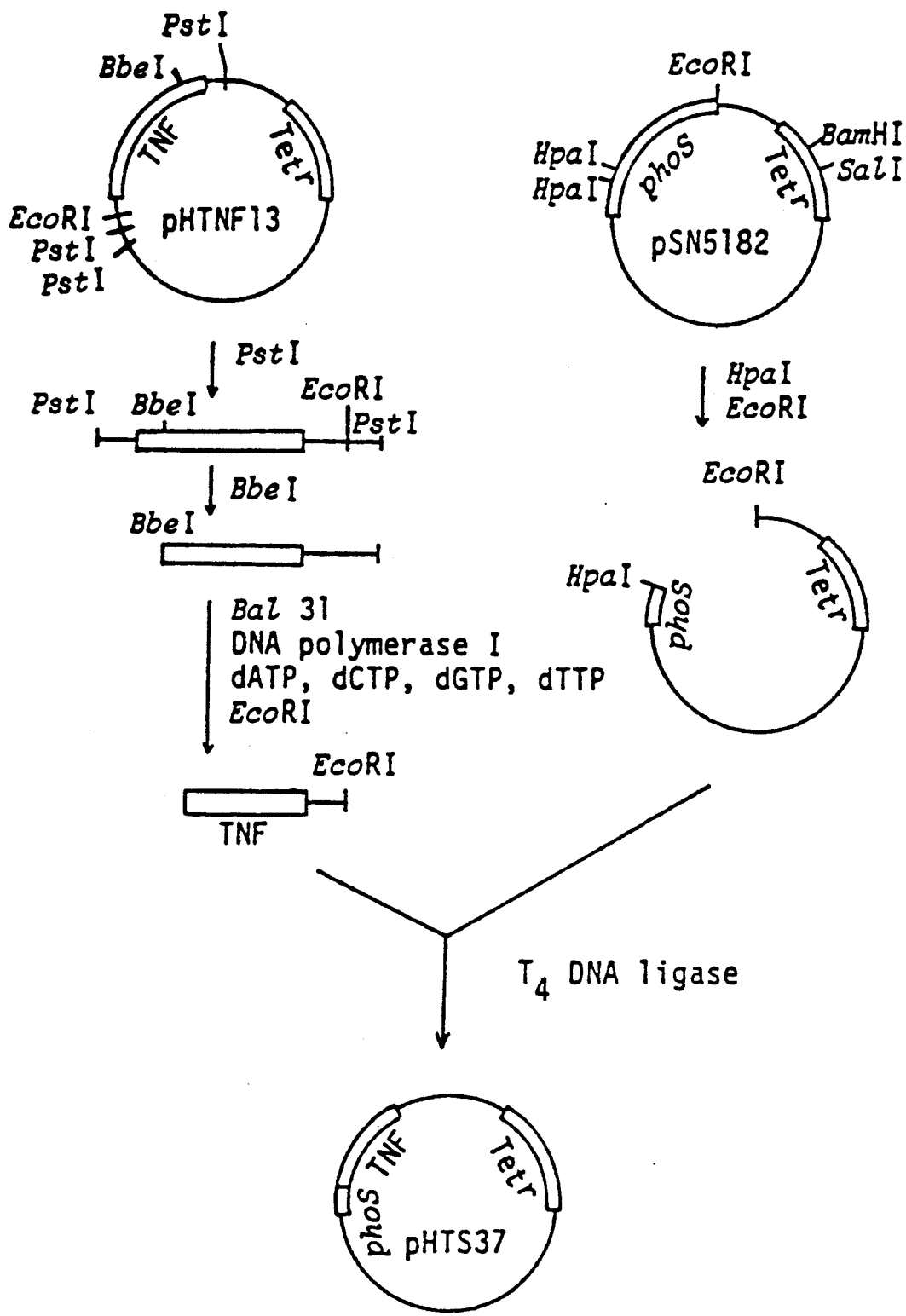

An expression plasmid pHTS37 capable of producing human TNF polypeptide fused with the signal peptide and the N-terminal portion of a phosphate binding protein and the mature human TNF polypeptide with a part of its precursor portion, and secreting the fused protein into the periplasm of host cells was constructed by the procedure illustrated in FIG. 5.

Recombinant plasmid (pHTNF13) DNA was digested with the restriction endonuclease PstI to cut out the DNA fragment (about 1.2 kbp) including human TNF cDNA. The DNA fragment was further digested with the restriction endonuclease BbeI to obtain a DNA fragment (about 0.9 kbp; to be referred to as BbeI-PstI fragment). Six micrograms of the BbeI-PstI fragment was dissolved in 80 microliters of 20 mM Trim-HCl (pH 8.0) buffer containing 12 mM CaCl$_2$, 12 mM MgCl$_2$, 0.2M NaCl, 1 mM EDTA and 0.02 unit of the exonuclease Bal 31, and incubated at 30° C. for 30 minutes to chew away about 50 to 150 base pairs from the both ends of the DNA fragment. Then the termini of the fragment were repaired by incubating at 37° C. for 60 minutes with 10 units of E. coli DNA polymerase I (large fragment) in the presence of 0.1 mM of each of four deoxyribonucleotide triphosphates, dGTP, dATP, dCTP and dTTP, and 50 micrograms/ml of bovine serum albumin. The repaired DNA fragment was digested with the restriction endonuclease EcoRI and resulting DNA fragment (about 750 bp) having a blunt end and a EcoRI cohesive end was isolated in a yield of about 3 micrograms (to be referred to as Bal 31-EcoRI fragment).

The Bal 31-EcoRI fragment was ligated with the HpaI-EcoRI fragment (about 4 kbp) obtained from pSN5182 as described in section (3) to construct an expression plasmid containing the phoS promoter region; Shine-Dalgarno sequence, the DNA sequence coding for the signal peptide and the N-terminal portion of a phosphate binding protein and the DNA sequence coding for the mature human TNF polypeptide and a part of its precursor polypeptide.

The expression plasmid was named pHTS37 and it was introduced into E. coli HB101 to obtain a transformant which was named HB101/pHTS37. The transformant HB101/pHTS37 was cultivated and the periplasmic extract was obtained under the same conditions as shown in section (3).

The periplasmic extract obtained had a cytotoxic activity of $4.93 \times 10^5$ units (L-929)/ml.

The extract was subjected to SDS-polyacrylamide gel (12.5%) electrophoresis. The electrophoresis was carried out at 35 V for 12 hours using Tris-glycine (pH 8.3) buffer containing 0.1% SDS. Protein was stained with Coomassie brilliant blue. Two protein bands, which were not observed in the extract of E. coli HB101, were detected at the positions corresponding to molecular weights of about 22,000 daltons and 16,500 daltons. Separately, the gel was sliced into 2 mm width and each gel was shaken in 1 ml of Eagle's minimum essential medium containing 1% fetal bovine serum at 4° C. overnight to elute proteins from the gel. Each eluate was used for determining the cytotoxic activity against mouse L-929 cells. As a result, a strong cytotoxic activity was detected in the eluate from the gel sliced from the position corresponding to the protein stained with Coomassie brilliant blue, which was determined to have a molecular weight of 16,500 daltons.

It was supposed from the structure of the expression plasmid pHTS37 that human TNF polypeptide produced in the transformant should be a fused protein of a part of phosphate binding protein and human TNF polypeptide with a part of its precursor portion. The theoretical molecular weight of the fused protein was calculated as about 23,000 daltons. On the other hand, the molecular weight of the mature human TNF polypeptide is 17,097 daltons. This investigation suggested that the fused protein produced could be converted to the mature human TNF polypeptide in the host cells by limited hydrolysis probably at a specific site (Arg-Ser) joining the mature human TNF polypeptide to its precursor portion.

When the periplasmic extract was incubated with 5 micrograms/ml of trypsin (from bovine pancreas, Sigma Chemical Co.) at 37° C. for 1 hour and the reaction mixture was subjected to SDS-polyacrylamide gel electrophoresis under the same conditions as above, a protein band detected at the position corresponding to a molecular weight of about 22,000 daltons, which might be the fused protein, disappeared by the trypsin digestion.

EXAMPLE 3

Production of modified human TNF polypeptide

An expression plasmid pHTRD4 carrying a DNA encoding a polypeptide resulting from deletion of four amino acids from the N-terminus of mature human TNF polypeptide was constructed according to the same strategy as that of the expression plasmid pHTR91 shown in Example 2-(2), except that the following synthetic adaptor was used instead of the adaptor I:

5'-CGATATGACC
3'-TATACTGGGGCT

By using the above synthetic adaptor, the base sequence followed by an initiation codon (ATG) is coding for an amino acid sequence consisting of 151 amino acid residues which results from deletion of 4 amino acids (Ser-Ser-Ser-Arg) from the N-terminal of the mature human TNF polypeptide.

The expression plasmid pHTRD4 constructed by the above procedure was introduced into E. coli HB101, and the transformant was cultivated overnight at 37° C. in the modified M-9 medium. The culture (0.05 ml) was inoculated in 5 ml of the same medium, and cultivated at 37° C. for 1 hour. Then, 3-beta-indoleacrylic acid was added to give a final concentration of 20 micrograms/ml and the cultivation was continued overnight. The cells were collected by centrifugation and treated by the same methods as described in Example 2-(1) to obtain a clarified lysate.

The lysate had a cytotoxic activity of $1.1 \times 10^5$ units (L-929)/ml.

EXAMPLE 4

Production of human TNF precursor polypeptide in Escherichia coli

An expression plasmid pHTRP3 carrying a cDNA encoding a human TNF precursor polypeptide consisting of 233 amino acids was constructed as follows: The cloned cDNA was isolated from the recombinant plasmid pHT113 by double digestion with the restriction endonucleases PstI and HindIII and the cDNA fragment was further digested partially with the restriction endonuclease HgiAI to obtain the DNA fragment (about 820 bp) including the base sequence encoding most of the precursor polypeptide. The resulting DNA fragment was ligated with a chemically synthesized oligodeoxyribonucleotide fragment represented by the following formula:

```
5'-CGATATGAGCA
3'-TATAC
```

The ligated DNA fragment was referred to as Pre-TNF fragment.

Separately, the DNA fragment containing a part of trp promoter region was cut out from plasmid pDR720 by digesting with the restriction endonucleases EcoRI and HpaI, and the DNA fragment was ligated with the following chemically synthesized adaptor.

```
5'-AACTAGTACGCAAGTTCACGTAAAAAGGGTAAT
3'-TTGATCATGCGTTCAAGTGCATTTTTCCCATTAGC
```

The resulting DNA fragment was ligated with the Pre-TNF fragment and the ligated DNA fragment was combined with the DNA fragment (about 4.3 kbp) having an ampicillin-resistance gene isolated from plasmid pBR322 by digesting with the restriction endonucleases EcoRI and HindIII.

The expression plasmid pHTRP3 constructed by the above procedure was introduced into *E. coli* HB101, and the transformant was cultivated overnight at 37° C. in the modified M-9 medium. The culture (0.05 ml) was inoculated in 5 ml of the same medium, and cultivated at 37° C. for 1 hour. Then, 3-beta-indoleacrylic acid was added to give a final concentration of 20 micrograms/ml, and the cultivation was continued overnight. The cells were collected by centrifugation and treated by the same methods as described in Example 2-(1) to obtain a clarified lysate.

The lysate had a cytotoxic activity of $1.8 \times 10^4$ units (L-929)/ml.

EXAMPLE 5

Production and purification of human TNF polypeptide

(1) Production in *Escherichia coli*

The transformant HB101/pHTR91 obtained in Example 2-(2) was used for the production of human TNF polypeptide. The transformant was cultivated overnight at 37° C. in LB broth supplemented with 12.5 micrograms/ml of tetracycline. The culture was inoculated into 10 volumes of the modified M-9 medium used in Example 2-(2), and cultivated at 37° C. for 1 hour. After adding 3-beta-indoleacrylic acid to give a final concentration of 20 micrograms/ml, the cultivation was continued for 4 hours. The cells were collected and treated to obtain a clarified lysate by the same method as shown in Example 2-(1). The lysate was used for the purification of human TNF polypeptide.

(2) Purification of human TNF polypeptide

Human TNF polypeptide was purified from the lysate obtained in section (1) by the following procedure. To a column (5×20 cm) packed with DEAE-Sepharose CL-6B (Pharmacia) previously equilibrated with 20 mM Tris-HCl (pH 7.8) buffer, 1030 ml of the lysate was applied. The column was washed with 3 liters of the same buffer, and then eluted with a linear gradient of NaCl from zero to 0.3M in the same buffer at a flow rate of 133 ml/hour. The eluate was fractionated into 10 ml-fractions. The fractions having cytotoxic activity were collected and pooled.

A recovery of a cytotoxic activity was 53% in this step, and a specific activity was increased up to about 9 times.

The pooled active fractions were desalted and concentrated to one-tenth volume by ultrafiltration with Diaflo using a YM10 membrane (Amicon).

The concentrate was subjected to preparative iso-electrofocusing gel electrophoresis. An aliquot of the concentrate was loaded onto a polyacrylamide gel plate (0.2×10×10 cm) with a pH gradient ranging from pH 5.6 to pH 6.1 created with Immobiline (LKB). The electrophoresis was carried out at 2,400 V for 16 hours at 15° C. The gel was sliced into 10-mm width and the protein was eluted with 20 mM Tris-HCl (pH 7.8) buffer. The above procedure was repeated. The eluates having cytotoxic activity were pooled and concentrated by ultrafiltration as above. Finally, the concentrate was applied onto a column (0.7×25 cm) of Bio-Gel P-6 (BIO-RAD) and desalted.

The desalted final preparation having cytotoxic activity was homogeneous on the basis of SDS-polyacrylamide gel electrophoretic analysis, and it was used as a purified human TNF polypeptide for analyses as mentioned in section [III].

EXAMPLE 6

Process for preparation of lyophilized human TNF polypeptide

The purified human TNF polypeptide solution obtained by the method described in Example 5 was used for preparation of a lyophilized human TNF polypeptide.

Ten milliliters of the purified human TNF polypeptide solution containing a cytotoxic activity of $2.2 \times 10^7$ units (LM) was mixed with one-tenth volume of 8% NaCl containing 10% human serum albumin and 20% D-mannitol. After adjusting pH of the solution to 6.8, the resulting solution was sterilized by filtration through Microflow membrane (Flow Labs., pore size 0.2 micron). Five milliliters of the sterile solution was dispensed into glass vials and then lyophilized. Each vial contains $10^7$ units (LM) of purified human TNF polypeptide.

REFERENTIAL EXAMPLE 1

Preparation of Rabbit TNF cDNA

(1) Preparation of TNF mRNA from macrophages of rabbit alveolus

Rabbits (weighing about 2.5 kg) were intravenously injected with killed dried cells of *Propionibacterium acnes* at a dose of 100 mg per rabbit, and sacrificed 8 days later. The lungs were repeatedly washed with phosphate buffered saline through a tube inserted into the trachea of the animals, and alveolar macrophages were collected. About $3 \times 10^9$ alveolar macrophages were obtained from 12 rabbits.

The alveolar macrophages were suspended in RPMI-1640 medium containing 10% fetal bovine serum, and seeded in Petri dishes (8 cm in diameter) at a cell density of $2 \times 10^7$ cells per dish. They were precultivated at 37° C. in a fully humidified atmosphere containing 5% carbon dioxide. After precultivation for one hour, endotoxin (lipopoly-saccharide derived from *E. coli*), TPA (phorbol-12-myristate-13-acetate) and cycloheximide (protein-synthesis inhibitor) were added so that their final concentrations became 10 micrograms/ml, 10 ng/ml and 1 microgram/ml, respectively. The cultivation was further continued for 4 to 4.5 hours (total of 5 to 5.5 hours), the culture medium was removed by suction, and the macrophages adhered to the dishes were lysed and homogenized in a SM guanidyl thiocyanate solution containing 0.6% sodium N-lauroyl sarcosinate and 6 mM sodium citrate. The homogenate was loaded on a 5.7M cesium chloride solution containing 0.1M EDTA, and centrifuged for 20 hours at 26,500 rpm using an ultracentrifuge (RPS27-2 rotor, Hitachi Koki) to obtain a total RNA fraction as pellets. The pellets were dissolved in a small amount of 7M urea solution containing 0.35M NaCl, 20 mM Tris-HCl (pH 7.4) and 20 mM EDTA and recovered by precipitation from ethanol. From 12 rabbits, 5.2 mg of total RNA were obtained.

The total RNA fraction was dissolved in 2 ml of TE solution used in Example 1-(1), and the solution was heated at 65° C. for 5 minutes. A NaCl solution was added to a final concentration of 0.5M, and the solution was applied onto a column of oligo(dT)-cellulose previously equilibrated with the TE solution containing 0.5M NaCl. Poly(A)mRNA was eluted from the column with the TE solution in an yield of 314 micrograms. Two hundred micrograms of the resulting poly(A)mRNA was subjected to agarose gel electrophoresis (gel concentration 1%, in the presence of 6M urea, pH 4), and fractionated into 7 fractions according to molecular sizes. Poly(A)mRNA was isolated from each gel fractionated by melting at 70° C. for 10 minutes followed by successive extraction with phenol and chloroform, and by precipitation from ethanol. The content of rabbit TNF mRNA in poly(A)mRNA recovered from each fraction was determined by a mRNA translation assay using oocytes of *Xenopus laevis*.

Rabbit TNF mRNA was recovered at a higher concentration from a fraction corresponding to a molecular size of 1.6 to 2.7 kb (to be abbreviated as an enriched rabbit TNF mRNA).

The enriched rabbit TNF mRNA fraction obtained herein was used in the following experiment.

(2) Synthesis of cDNA cDNA was synthesized under the following conditions. Four micrograms of the enriched TNF mRNA fraction was dissolved in 100 microliters of 50 mM Tris-HCl (pH 8.3) buffer containing 10 mM $MgCl_2$, 70 mM KCl, 1 mM dithiothreitol, 0.5 mM of each of the four deoxyribonucleotide triphosphates, dTTP, dCTP, dATP and dGTP (dCTP was labelled with $^{32}P$; specific activity, $4.4 \times 10^6$ cpm/nmole), 3 micrograms of oligo(dt)$_{12-18}$ and 80 units of reverse transcriptase derived from avian myeloblastosis virus and incubated at 43° C. for 90 minutes. Then the reaction was stopped by adding EDTA. The resulting cDNA-mRNA hybrid was extracted with phenol/chloroform (1:1), and recovered from the aqueous phase by precipitation from ethanol. The mRNA template was removed by treating with an alkali at 65° to 70° C. The synthesized sscDNA was recovered by precipitation from ethanol.

The sscDNA precipitate was dissolved in 40 microliters of a 0.1M Hepes (pH 6.9) buffer containing 0.5 mM of each of the four deoxyribonucleotide triphosphates, dATP, dTTP, dGTP and dCTP, 5 mM $MgCl_2$, 70 mM KCl, 1.5 mM 2-mercaptoethanol, and 8 units of *E. coli* DNA polymerase I (large fragment), and incubated at 15° C. for 20 hours to synthesize dscDNA. The reaction was stopped by adding sodium dodecylsulfate. The dscDNA was extracted with phenol/chloroform, and recovered by precipitation from ethanol.

The resulting dscDNA was dissolved in 100 microliters of 50 mM sodium acetate (pH 4.5) containing 1 mM few $ZnSO_4$, 200 mM NaCl, 0.5% glycerol and 0.5 unit of S1 nuclease and incubated at 37° C. for 20 minutes to cleave the hairpin structure. The reaction was stopped by adding EDTA. The reaction mixture was extracted with phenol/chloroform and then with diethyl ether. dscDNA was recovered by precipitation from ethanol.

(3) Preparation of oligo(dC)-tailed cDNA

The dscDNA obtained as above was dissolved in 100 microliters of 130 mM sodium cacodylate-30 mM Tris-HCl (pH 6.8) buffer containing 1 mM $CoCl_2$, 0.1 mM dithiothreitol, 0.2 microgram of poly(A), 0.1 mM $^3$H-dCTP (specific activity, 5400 cpm/pmole) and 10 units of terminal deoxynucleotidyl transferase and incubated at 37° C. for 20 minutes to permit the addition of oligo(dc) tails to the 3'-termini of dscDNA.

The reaction was stopped by adding EDTA. The reaction mixture was extracted with phenol/chloroform and then with diethyl ether, and the oligo(dC)-tailed dscDNA was recovered by precipitation from ethanol. The oligo-(dc)-tailed dscDNA was dissolved in 10 mM Tris-HCl (pH 7.4) buffer containing 1 mM EDTA and 100 mM NaCl so that it contained 0.2 microgram of the oligo(dC)-tailed dscDNA per ml.

(4) Preparation of oligo(dG)-tailed plasmid pBR322 DNA pBR322 (10 micrograms) was dissolved in 100 microliters of 20 mM Tris-HCl (pH 7.4) buffer containing 10 mM $MgCl_2$, 50 mM $(NH_4)_2SO_4$ and 10 micrograms of bovine serum albumin, and 15 units of restriction endonuclease PstI was added. The mixture was incubated at 37° C. for 1 hour. After the reaction was terminated, the reaction mixture was extracted with phenol/chloroform, and the resulting DNA was recovered from the aqueous phase by precipitation from ethanol. The DNA obtained was dissolved in 200 microliters of the same reaction buffer as used in tailing of the dscDNA above (except that it contained 80 units of terminal deoxynucleotidyl transferase and $^3$H-dGTP instead of $^3$H-dCTP) and incubated at 37° C. for 20 minutes to add about 10-15 dG residues per end. The reaction mixture was extracted with phenol/chloroform, and the oligo(dG)tailed plasmid pBR322 DNA was recovered from the aqueous phase by ethanol precipitation. The resulting tailed plasmid DNA was dissolved in the same buffer as used in dissolving the oligo(dC)-tailed dscDNA so that it contained the tailed plasmid DNA in a concentration of 2 micrograms per ml.

(5) Construction of a recombinant plasmid

Fifty microliters of the oligo(dC)-tailed cDNA solution was mixed with 50 microliters of the oligo(dG)tailed pBR322 DNA solution, and the mixture was incubated sequentially at 65° C. for 10 minutes, at 57° C. for 120 minutes, at 45° C. for 60 minutes, at 35° C. for 60 minutes and at room temperature for 60 minutes to perform annealing and to construct recombinant plasmids.

(6) Selection of transformants

E. coli χ1776 strain was transformed with the recombinant plasmids obtained as above.

Specifically, E. coli χ1776 was cultivated at 37° C. in 20 ml of L broth supplemented with 100 micrograms/ml of diaminopimelic acid and 40 micrograms/ml of thymidine until the turbidity at 600 nm reached 0.5. The cells were collected by centrifugation at 0° C., and washed with 10 mM Tris-HCl (pH 7.3) buffer containing 50 mM $CaCl_2$. The cells were resuspended in 2 ml of the same buffer as used above, and left to stand at 0° C. for 5 minutes. To 0.2 ml of the suspension was added 0.1 ml of the recombinant plasmid solution obtained as above. The mixture was left to stand at 0° C. for 15 minutes and then maintained at 42° C. for 2 minutes. Then, 0.5 ml of the supplemented L broth used above was added, and cultivation was carried out with shaking for 1 hour. An aliquot of the culture was taken, spread on the supplemented L broth agar plate containing 15 micrograms/ml of tetracycline, and cultivated at 37° C. for about 12 hours. Transformants resistant to tetracycline were selected, which were used as a cDNA library.

(7) Hybridization assay

Colony hybridization assay was conducted using a $^{32}P$-labelled cDNA probe by the method of Hanahan and Meselson in order to screen the cDNA library for transformants which had a plasmid containing cDNA encoding rabbit THF. Induction plus and induction minus $^{32}P$-labelled sscDNA probes were synthesized by the method described in section (2) above using mRNAs obtained from induction plus and minus alveolar macrophages by the method described in section (1) except that $^{32}P$-dCTP with high specific radioactivity was used. By this test, there were selected colonies of transformants harboring the recombinant plasmids which strongly hybridized with the induction plus probe but did not hybridize with the induction minus probe. Fifty colonies were selected from about 20,000 colonies.

Twenty out of the selected 50 colonies were then subjected to a mRNA hybridization-translation assay by the method described in T. Maniatis et al. (ed) "Molecular Cloning", 329 (1980), Cold Spring Harbor Lab. The plasmid DNA was extracted from each of the transformants and fixed to nitrocellulose filters after heat denaturation. The poly(A)mRNA fraction containing rabbit TNF mRNA obtained in section (1) above was added to the filter and incubated at 50° C. for 3 hours to perform hybridization. The hybridized mRNA was recovered and injected into the oocytes to determine whether the recovered mRNA was rabbit TNF mRNA. As a result of this test, three colonies were found to have plasmids containing cDNAs that strongly hybridized with the rabbit TNF mRNA. cDNA fragments were obtained from the plasmid having cDNA of the largest size (about 750 bp) by digestion with the restriction endonuclease DdeI, and used as a probe for further screening. These DNA fragments were labelled with $^{32}P$. By using these probes, the cDNA library obtained in section (6) above was screened by a colony hybridization assay, and colonies of transformants having plasmids containing cDNAs which strongly hybridized with the labelled probes were selected. Ninety-eight colonies out of about 60,000 colonies of the cDNA library were found to be positive in this test. The recombinant plasmid DNA was isolated and cDNA inserts were cut out from these recombinant plasmids by digestion with the restriction endonuclease PstI, and their sizes were measured by polyacrylamide gel electrophoresis. Seventeen clones of transformants having cDNA inserts of at least 1 kbp were selected. From a transformant containing cDNA of the largest size (transformant No: χ1776/pRTNF802; plasmid No.: pRTNF802), the cloned cDNA was isolated, and its base sequence was determined by the following method.

(8) Determination of the base sequence of the cloned cDNA

The tranformant χ1776/PRTNF802 selected in section (7) above was cultivated in L broth supplemented with diaminopimelic acid and thymidine. The cells were treated in accordance with the method of Wilkie et al. to obtain a plasmid DNA. The plasmid DNA was digested with the restriction endonuclease PstI, and purified to obtain a cloned cDNA. The cloned cDNA fragment was further digested with various restriction endonucleases, and the base sequences of suitable restriction endonuclease-cleaved fragments were determined by Maxam-Gilbert method.

The base sequence determined is shown in Table 9 below. The base sequence of the 277th to 738th bases were assigned to the coding region for mature rabbit TNF according to the N-terminal and C-terminal amino acid sequences of TNF purified from rabbit plasma elucidated in Referential Example 2. The 34th to 276th bases constitute a base sequence which is presumed to encode a polypeptide required for constituting a precursor of rabbit TNF.

REFERENTIAL EXAMPLE 2

Isolation and purification of rabbit plasma TNF

Rabbits (body weighing 2.5 to 3.0 kg) were injected intravenously with 50 mg of killed dried cells of *Propionibacterium acnes*. Eight days later, the rabbits were intravenously injected with 100 micrograms of endotoxin (lipopolyeaccharide derived from *E. coli*). Two hours later, blood was taken from each rabbit by cardiac puncture. The blood was mixed with 100 units of sodium heparin per 100 ml, and then centrifuged at 5,000 rpm for 30 minutes under cooling to remove blood cells and insoluble matters. Twenty-four liters of the plasma was obtained from 400 rabbits.

EDTA (24 g) and 240 g of celite were added to 24 liters of the plasma, and the mixture was stirred for 1 hour and then filtered successively through filters having a pore size of 3 microns, 1 micron and 0.2 micron.

To 24 liters of the filtrate was added 12 liters of 0.04M Tris-HCl (pH 7.8) buffer, and the mixture was applied onto a column (27×45 cm) of DEAE-Sepharose CL-6B (Pharmacia) equilibrated with 0.04M Tris-HCl (pH 7.8) buffer containing 0.1M NaCl. The column was then washed with 75 liters of 0.04M Tris-HCl (pH 7.8) buffer containing 0.1M NaCl and then with 50 liters of 0.04M Tris-HCl (pH 7.8) buffer containing 0.15M NaCl, and then eluted with 0.04M Tris-HCl (pH 7.2) buffer containing 0.18M NaCl. The eluate was fractionated into 8-liter fractions, and active fractions having cytotoxic activity were collected. The active fractions were pooled and diluted with an equal volume of 0.04M Tris-HCl (pH 7.8) buffer. The diluted solution was applied onto a column (10×13 cm) of DEAE-Sepharose CL-6B. The column was washed with 1 liter of 0.04M Tris-HCl (pH 7.8) buffer containing 0.1M NaCl and then eluted with 5 liters of 0.04M Tris-HCl (pH 7.2) buffer containing 0.18M NaCl. The eluate was fractionated into 250 ml fractions and fractions having cytotoxic activity were collected and pooled.

The active fraction was heated at 60° C. for 30 minutes and rapidly cooled to 4° C. The cooled solution was concentrated by ultrafiltration.

The resulting concentrate was applied onto a column (5×80 cm) of Sephacryl S-200 (Pharmacia) equilibrated with 0.005M phosphate (pH 7.4) buffer containing 0.1M NaCl, and eluted with the same buffer. The eluate was fractionated into 40 ml fractions, and active fractions were collected, pooled and concentrated by ultrafiltration.

The concentrate of the active fraction obtained by gel filtration was applied onto a column of $Zn^{2+}$ chelate Sepharose as shown below. A column (1.6×20 cm) filled with chelate Sepharose (iminodiacetic acid fixed resin) prepared by the method of J. Porath et al., [Nature, 258, 598 (1975)] was washed with 120 ml of zinc chloride solution (1 mg/ml) and then equilibrated with 0.05M phosphate (pH 7.4) buffer containing 0.1M NaCl. Then, the concentrate obtained in the previous step was applied onto the column, and eluted with the same buffer. Fractions not adsorbed on the column were collected. Cytotoxic activity was almost completely recovered in these fractions.

The active fractions obtained in the previous step were concentrated and applied onto a column (1.5×90 cm) of Toyopearl HW-55 (Toyo Soda Co., Ltd.) fully equilibrated with 0.005M phosphate (pH 7.4) buffer containing 0.15M NaCl. The column was eluted with the same buffer, and active fractions were pooled. This preparation was a purified rabbit plasma TNF.

This purified rabbit plasma TNF obtained herein was used in Referential Examples 3 and 4.

REFERENTIAL EXAMPLE 3

Determination of N-terminal and C-terminal amino acid sequences of rabbit plasma TNF The purified rabbit plasma TNF obtained in Referential Example 2 was used for the determination of the N-terminal and C-terminal amino acid sequences.

The N-terminal amino acid sequence was determined by the Edman degradation method. The resulting phenylthiohydantoin-amino acids were identified by high-performance liquid chromatography using a Zorbax ODS column (Du Pont).

The C-terminal amino acid sequence was determined by the enzymatic method using carboxypeptidases. The purified rabbit plasma TNF was digested with the carboxypeptidases A and Y, at molar ratios of enzyme to substrate of 1:25 and 1:1,000 respectively. The free amino acids released from the C-terminus of rabbit plasma TNF by the double digestion were identified by a micro-amino acid analyzer (Shimadzu Seisakusho) at appropriate intervals from 2 minutes to 180 minutes after the digestion.

It was consequently found that the N-terminal and C-terminal amino acid sequences of rabbit plasma TNF were as follows:

N-terminal: Ser—Ala—Ser—Arg—Ala— ...
C-terminal: ... Val—Tyr—Phe—Gly—Ile—Ile—Ala—Leu

REFERENTIAL EXAMPLE 4

Preparation of an anti-rabbit plasma TNF antibody

TNF solution containing $1.9 \times 10^5$ units (L-929) of the purified rabbit plasma TNF obtained in Referential Example 2 was emulsified with an equal volume of the Freund's complete adjuvant, and the emulsion was injected subcutaneously into the back of guinea pigs at several parts. Then, the animals were immunized by the same method 1, 3 and 6 weeks later. Furthermore, 8 weeks later, the same amount of the purified rabbit plasma TNF was intraperitoneally injected together with aluminum hydroxide gel. The whole blood was taken by cardiac puncture 9 weeks after the first immunization, and centrifuged to obtain an antiserum containing an anti-rabbit plasma TNF antibody.

The antiserum was passed through a column of Sepharose 4B coupled with serum protein components of normal rabbits. By repeating it 3 times a purified antibody specific for the rabbit plasma TNF was obtained. It was confirmed by immunoelectrophoresis and gel double diffusion methods that this antibody formed a single precipitation line only with the purified rabbit plasma TNF.

An about 60,000-fold dilution of this purified antibody has the ability of neutralizing 50% of 500 units (L-929) of the cytotoxic activity of the rabbit plasma TNF, and an about 1,000-fold dilution of the antibody can completely neutralize 50 units (LM) of the cytotoxic activity of the rabbit plasma TNF.

What is claimed is:

1. A polypeptide having human tumor necrosis factor activity and being selected from the group consisting of
   (a) the polypeptide having the amino acid sequence of the following formula, and
   (b) a polypeptide having an amino acid sequence resulting from the addition of one or two amino acid residues from the precursor portion of said polypeptide (a) to the N-terminus of the following formula:

| | | | | Ser | Ser | Ser | Arg |
|---|---|---|---|---|---|---|---|
| Thr | Pro | Ser | Asp | Lys | Pro | Val | Ala | His | Val |
| Val | Ala | Asn | Pro | Gln | Ala | Glu | Gly | Gln | Leu |
| Gln | Trp | Leu | Asn | Arg | Arg | Ala | Asn | Ala | Leu |
| Leu | Ala | Asn | Gly | Val | Glu | Leu | Arg | Asp | Asn |
| Gln | Leu | Val | Val | Pro | Ser | Glu | Gly | Leu | Tyr |
| Leu | Ile | Tyr | Ser | Gln | Val | Leu | Phe | Lys | Gly |
| Gln | Gly | Cys | Pro | Ser | Thr | His | Val | Leu | Leu |
| Thr | His | Thr | Ile | Ser | Arg | Ile | Ala | Val | Ser |
| Tyr | Gln | Thr | Lys | Val | Asn | Leu | Leu | Ser | Ala |
| Ile | Lys | Ser | Pro | Cys | Gln | Arg | Glu | Thr | Pro |
| Glu | Gly | Ala | Glu | Ala | Lys | Pro | Trp | Tyr | Glu |
| Pro | Ile | Tyr | Leu | Gly | Gly | Val | Phe | Gln | Leu |
| Glu | Lys | Gly | Asp | Arg | Leu | Ser | Ala | Glu | Ile |
| Asn | Arg | Pro | Asp | Tyr | Leu | Asp | Phe | Ala | Glu |
| Ser | Gly | Gln | Val | Tyr | Phe | Gly | Ile | Ile | Ala |
| Leu. | | | | | | | | | |

2. A human tumor necrosis factor polypeptide claimed in claim 1 having the following amino acid sequence:

| Ser | Ser | Ser | Arg | Thr | Pro | Ser | Asp | Lys | Pro |
|---|---|---|---|---|---|---|---|---|---|
| Val | Ala | His | Val | Val | Ala | Asn | Pro | Gln | Ala |
| Glu | Gly | Gln | Leu | Gln | Trp | Leu | Asn | Arg | Arg |
| Ala | Asn | Ala | Leu | Leu | Ala | Asn | Gly | Val | Glu |
| Leu | Arg | Asp | Asn | Gln | Leu | Val | Val | Pro | Ser |
| Glu | Gly | Leu | Tyr | Leu | Ile | Tyr | Ser | Gln | Val |
| Leu | Phe | Lys | Gly | Gln | Gly | Cys | Pro | Ser | Thr |
| His | Val | Leu | Leu | Thr | His | Thr | Ile | Ser | Arg |

-continued

| | | | | | | | | |
|---|---|---|---|---|---|---|---|---|
| Ile | Ala | Val | Ser | Tyr | Gln | Thr | Lys | Val | Asn |
| Leu | Leu | Ser | Ala | Ile | Lys | Ser | Pro | Cys | Gln |
| Arg | Glu | Thr | Pro | Glu | Gly | Ala | Glu | Ala | Lys |
| Pro | Trp | Tyr | Glu | Pro | Ile | Tyr | Leu | Gly | Gly |
| Val | Phe | Gln | Leu | Glu | Lys | Gly | Asp | Arg | Leu |
| Ser | Ala | Glu | Ile | Asn | Arg | Pro | Asp | Tyr | Leu |
| Asp | Phe | Ala | Glu | Ser | Gly | Gln | Val | Tyr | Phe |
| Gly | Ile | Ile | Ala | Leu. | | | | | |

3. A human tumor necrosis factor precursor polypeptide having the following amino acid sequence:

| | | | | | | | | |
|---|---|---|---|---|---|---|---|---|
| Ser | Thr | Glu | Ser | Met | Ile | Arg | Asp | Val | Glu |
| Leu | Ala | Glu | Glu | Ala | Leu | Pro | Lys | Lys | Thr |
| Gly | Gly | Pro | Gln | Gly | Ser | Arg | Arg | Cys | Leu |
| Phe | Leu | Ser | Leu | Phe | Ser | Phe | Leu | Ile | Val |
| Ala | Gly | Ala | Thr | Thr | Leu | Phe | Cys | Leu | Leu |
| His | Phe | Gly | Val | Ile | Gly | Pro | Gln | Arg | Glu |
| Glu | Phe | Pro | Arg | Asp | Leu | Ser | Leu | Ile | Ser |
| Pro | Leu | Ala | Gln | Ala | Val | Arg | Ser | Ser | Ser |
| Arg | Thr | Pro | Ser | Asp | Lys | Pro | Val | Ala | His |
| Val | Val | Ala | Asn | Pro | Gln | Ala | Glu | Gly | Gln |
| Leu | Gln | Trp | Leu | Asn | Arg | Arg | Ala | Asn | Ala |
| Leu | Leu | Ala | Asn | Gly | Val | Glu | Leu | Arg | Asp |
| Asn | Gln | Leu | Val | Val | Pro | Ser | Glu | Gly | Leu |
| Tyr | Leu | Ile | Tyr | Ser | Gln | Val | Leu | Phe | Lys |
| Gly | Gln | Gly | Cys | Pro | Ser | Thr | His | Val | Leu |
| Leu | Thr | His | Thr | Ile | Ser | Arg | Ile | Ala | Val |
| Ser | Tyr | Gln | Thr | Lys | Val | Asn | Leu | Leu | Ser |
| Ala | Ile | Lys | Ser | Pro | Cys | Gln | Arg | Glu | Thr |
| Pro | Glu | Gly | Ala | Glu | Ala | Lys | Pro | Trp | Tyr |
| Glu | Pro | Ile | Tyr | Leu | Gly | Gly | Val | Phe | Gln |
| Leu | Glu | Lys | Gly | Asp | Arg | Leu | Ser | Ala | Glu |
| Ile | Asn | Arg | Pro | Asp | Tyr | Leu | Asp | Phe | Ala |
| Glu | Ser | Gly | Gln | Val | Tyr | Phe | Gly | Ile | Ile |
| Ala | Leu | | | | | | | | | or the said polypeptide having a methionine residue at the N-terminus.

4. A pharmaceutical composition which comprises an anti-tumor effective amount of a polypeptide as defined in claim 1 as an active ingredient and a vehicle or a stabilizer therefor.

* * * * *

Adverse Decisions In Interference

Patent No. 5,288,852, Masaaki Yamada, HUMAN TUMOR NECROSIS FACTOR POLYPEPTIDES, Interference No. 103,605, final judgment adverse to the patentees rendered July 30, 1999, as to claims 1 and 4.

*(Official Gazette June 13, 2000)*

Adverse Decisions In Interference

Patent No. 5,288,852, Masaaki Yamada, HUMAN TUMOR NECROSIS FACTOR POLYPEPTIDES, Interference No. 103,605, final judgment adverse to the patentees rendered July 30, 1999 as to claims 1 and 4.

*(Official Gazette July 4, 2000)*

Adverse Decision In Interference

Patent No. 5,288,852, Masaaki Yamada, Yasuji Furutani, Mitsue Notake, Juniti Yamagishi, HUMAN TUMOR NECROSIS FACTOR POLYPEPTIDES, Interference No. 103,605, final judgment adverse to the patentees rendered July 30, 1999, as to claims 1 and 4.

*(Official Gazette September 18, 2001)*